US011446355B2

(12) United States Patent
Lovejoy et al.

(10) Patent No.: US 11,446,355 B2
(45) Date of Patent: Sep. 20, 2022

(54) COMPOSITIONS, METHODS AND USES COMPRISING TENEURIN C-TERMINAL ASSOCIATED PEPTIDE -1 (TCAP-1) FOR ENHANCING MUSCLE PERFORMANCE

(71) Applicants: David Lovejoy, Stouffville (CA); Andrea D'Aquila, Oakville (CA); Marius Locke, Toronto (CA)

(72) Inventors: David Lovejoy, Stouffville (CA); Andrea D'Aquila, Oakville (CA); Marius Locke, Toronto (CA)

( * ) Notice: Subject to any disclaimer, the term of this patent is extended or adjusted under 35 U.S.C. 154(b) by 0 days.

(21) Appl. No.: 16/336,334

(22) PCT Filed: Sep. 26, 2017

(86) PCT No.: PCT/CA2017/051136
§ 371 (c)(1),
(2) Date: Mar. 25, 2019

(87) PCT Pub. No.: WO2018/053653
PCT Pub. Date: Mar. 29, 2018

(65) Prior Publication Data
US 2019/0216890 A1    Jul. 18, 2019

Related U.S. Application Data

(60) Provisional application No. 62/399,702, filed on Sep. 26, 2016.

(51) Int. Cl.
*A61P 21/00* (2006.01)
*A61K 38/17* (2006.01)
*C07K 14/705* (2006.01)
*C07K 14/47* (2006.01)
*A61K 9/00* (2006.01)

(52) U.S. Cl.
CPC ............ *A61K 38/17* (2013.01); *A61K 9/0019* (2013.01); *A61K 38/1709* (2013.01); *A61P 21/00* (2018.01); *C07K 14/47* (2013.01); *C07K 14/705* (2013.01)

(58) Field of Classification Search
None
See application file for complete search history.

(56) References Cited

FOREIGN PATENT DOCUMENTS

WO    2016/008034    1/2016

OTHER PUBLICATIONS

Lars Larsson, et al., Sarcopenia: Aging-Related Loss of Muscle Mass and Function, Physiol Rev. Jan. 1, 2019; 99(1): 427-511 (Year: 2019).*

Ferreiro, A. et al. Telethonin-deficiency initially presenting as a congenital muscular dystrophy. Neuromuscul Disord., 2011, 21(6): 433-438, ISSN 1873-2364.
Ibrahim, M. et al., A critical role for telethonin in regulating t-tubule structure and function in the mammalian heart. Hum Mol Genet., 2013, 22(2): 372-383, ISSN 1460-2083.
PCT Search Report & Written Opinion dated Nov. 3, 2017, Application No. PCT/CA2017/051136.
PCT International Preliminary Report on Patentability dated Mar. 26, 2019 (International Application No. PCT/CA2017/051136).
Al Chawaf, A., Xu, K., Tan, L., Vaccarino, F. J., Lovejoy, D. A., & Rotzinger, S. (2007). Corticotropin-releasing factor (CRF)-induced behaviors are modulated by intravenous administration of teneurin C-terminal associated peptide-1 (TCAP-1). http://doi.orq/10.1016/j.peptides.2007.05.014.
Allen, D. G., Lamb, G. D., & Westerblad, H. (2008). Skeletal muscle fatigue: cellular mechanisms. Physiological Reviews, 88(1), 287-332. http://doi.org/10.1152/physrev.00015.2007.
Bellinger, A. M., Mongillo, M., & Marks, A. R. (2008). Review series Stressed out: the skeletal muscle ryanodine receptor as a target of stress. Journal of Clinical Investigation, 118(2), 445-453. http://doi.org/10.1172/JCI34006. effects.
Boucard, A. A., Maxeiner, S., & Sudhof, T. C. (2014). Latrophilins function as heterophilic cell-adhesion molecules by binding to teneurins: Regulation by alternative splicing. Journal of Biological Chemistry, 289(1), 387-402. http://doi.org/10.1074/jbc.M113.504779.
Chand, D., Song, L., Delannoy, L., Barsyte-Lovejoy, D., Ackloo, S., Boutros, P. C., . . . Lovejoy, D. A. (2012). C-terminal region of teneurin-1 co-localizes with dystroglycan and modulates cytoskeletal organization through an extracellular signal-regulated kinase-dependent stathmin- and filamin A-mediated mechanism in hippocampal cells. Neuroscience, 219, 255-270. http://doi.org/10.1016/j.neuroscience.2012.05.069.
Chand, D., Casatti, C. A., de Lannoy, L., Song, L., Kollara, A., Barsyte-Lovejoy, D., . . . Lovejoy, D. A. (2013). C-terminal processing of the teneurin proteins: Independent actions of a teneurin C-terminal associated peptide in hippocampal cells. Molecular and Cellular Neuroscience, 52, 38-50. http://doi.org/10.1016/j.mcn.2012.09.006.
Chand, D., Colacci, M., Dixon, K., Kollara, A., Brown, T. J., & Lovejoy, D. A. (2014). C-terminal region of teneurin-1 co-localizes with the dystroglycan complex in adult mouse testes and regulates testicular size and testosterone production. Histochemistry and Cell Biology, 141 (2), 191-211. http://doi.org/10.1007/s00418-013-1154-1.
Chen, Y., Xu, M., Almeida, R. De, & Lovejoy, D. A. (2013). Teneurin C-terminal associated peptides (TCAP): Modulators of corticotropin-releasing factor (CRF) physiology and behavior. Frontiers in Neuroscience, 7(Sep. 7), 1-6. http://doi.org/10.3389/fnins.2013.00166.
Davletov, B. A., Meunier, F. A., Ashton, A. C., Matsushita, H., Hirst, W. D., Lelianova, V. G., . . . Ushkaryov, Y. A. (1998). Vesicle exocytosis stimulated by α-latrotoxin is mediated by latrophilin and requires both external and stored Ca2+. EMBO Journal, 17(14), 3909-3920. http://doi.org/10.1093/emboj/17.14.3909.

(Continued)

*Primary Examiner* — Thomas S Heard
(74) *Attorney, Agent, or Firm* — The Dobrusin Law Firm, P.C.

(57) ABSTRACT

The present matter relates to compositions comprising Teneurin C-terminal Associated Peptide-1 (TCAP-1) and methods and uses of same for enhancing and/or restoring muscle function.

17 Claims, 10 Drawing Sheets
Specification includes a Sequence Listing.

(56) References Cited

OTHER PUBLICATIONS

Holwerda, A. M., & Locke, M. (2014). Hsp25 and Hsp72 content in rat skeletal muscle following controlled shortening and lengthening contractions. Applied Physiology, Nutrition, and Metabolism, 39(12), 1380-1387. http://doi.org/10.1139/apnm-2014-0118.

Kenzelmann, D., Chiquet-Ehrismann, R., & Tucker, R. P. (2007). Teneurins, a transmembrane protein family involved in cell communication during neuronal development. Cellular and Molecular Life Sciences, 64(12), 1452-1456. http://doi.org/10.1007/s00018-007-7108-9.

Kupferschmidt, D. A., Lovejoy, D. A., Rotzinger, S., & Erb, S. (2011). Teneurin C-terminal associated peptide-1 blocks the effects of corticotropin-releasing factor on reinstatement of cocaine seeking and on cocaine-induced behavioural sensitization. British Journal of Pharmacology, 162(3), 574-583. http://doi.org/10.1111/j.1476-5381.2010.01055.x.

Maher, F., Davies-Hill, T. M., Lysko, P. G., Henneberry, R. C., & Simpson, I. a. (1991). Expression of two glucose transporters, GLUT1 and GLUT3, in cultured cerebellar neurons: Evidence for neuron-specific expression of GLUT3. Molecular and Cellular Neurosciences, 2(4), 351-60. http://doi.org/10.1016/1044-7431(91)90066-W.

Rahman, M. A., Ashton, A. C., Meunier, F. A., Davletov, B. A., Dolly, J. O., & Ushkaryov, Y. A. (1999). Norepinephrine exocytosis stimulated by alpha-latrotoxin requires both external and stored Ca2+ and is mediated by latrophilin, G proteins and phospholipase C. Philosophical Transactions of the Royal Society of London. Series B, Biological Sciences, 354(1381), 379-86. http://doi.org/10.1098/rstb.1999.0390.

Richter, E. A., & Hargreaves, M. (2013). Exercise, glut4, and skeletal muscle glucose uptake, (FIG. 2), 993-1017. http://doi.org/10.1152/physrev.00038.2012.

Santos, J. M., Ribeiro, S. B., Gaya, A. R., Appell, H. J., & Duarte, J. A. (2008). Skeletal muscle pathways of contraction-enhanced glucose uptake. International Journal of Sports Medicine, 29(10), 785-794. http://doi.org/10.1055/s-2008-1038404.

Silva, J.-P., Lelianova, V. G., Ermolyuk, Y. S., Vysokov, N., Hitchen, P. G., Berninghausen, O., Ushkaryov, Y. A. (2011). Latrophilin 1 and its endogenous ligand Lasso/teneurin-2 form a high-affinity transsynaptic receptor pair with signaling capabilities. Proceedings of the National Academy of Sciences of the United States of America, 108(29), 12113-8. http://doi.org/10.1073/pnas.1019434108.

Tan, L. A., Al Chawaf, A., Vaccarino, F. J., Boutros, P. C., & Lovejoy, D. A. (2011). Teneurin C-terminal associated peptide (TCAP)-1 modulates dendritic morphology in hippocampal neurons and decreases anxiety-like behaviors in rats. Physiology and Behavior, 104(2), 199-204, http://doi.org/10.1016/j.physbeh.2011.03.015.

Tan, L. A., Xu, K., Vaccarino, F. J., Lovejoy, D. A., & Rotzinger, S. (2009). Teneurin C-terminal associated peptide (TCAP)-1 attenuates corticotropin-releasing factor (CRF)-induced c-Fos expression in the limbic system and modulates anxiety behavior in male Wistar rats. Behavioural Brain Research, 201, 198-206. http://doi.org/10.1016/j.bbr.2009.02.013.

Trubiani, G., Al Chawaf, A., Belsham, D. D., Barsyte-Lovejoy, D., & Lovejoy, D. A. (2007). Teneurin carboxy (C)-terminal associated peptide-1 inhibits alkalosis-associated necrotic neuronal death by stimulating superoxide dismutase and catalase activity in immortalized mouse hypothalamic cells. Brain Research, 1176(1), 27-36. http://doi.org/10.1016/j.brainres.2007.07.087.

Uemura, E., & Greenlee, H. W. (2006). Insulin regulates neuronal glucose uptake by promoting translocation of glucose transporter GLUT3. Experimental Neurology, 198(1), 48-53. http://doi.org/10.1016/j. expneurol.2005.10.035.

Wang, L., Rotzinger, S., Al Chawaf, A., Elias, C. F., Barsyte-Lovejoy, D., Qian, X., . . . Lovejoy, D. A. (2005). Teneurin proteins possess a carboxy terminal sequence with neuromodulatory activity. Molecular Brain Research, 133(2), 253-265. http://doi.org/10.1016/j.molbrainres.2004.10.019.

Woelfle, R., D'Aquila, A. L., Pavlovic, T., Husic, M., Lovejoy, D. A. (2015). Ancient interaction between the teneurin C-terminal associated peptides (TCAP) and latrophilin ligand-receptor coupling: a role in behavior, 9(April), 1-10. http://doi.org/10.3389/fnins.2015.00146.

Zurlo, F., Larson, K., Bogardus, C., & Ravussin, E. (1990). Skeletal muscle metabolism is a major determinant of resting energy expenditure. Journal of Clinical Investigation, 86(5), 1423-1427. http://doi.org/10.1172/JCI114857.

* cited by examiner

| | |
|---|---|
| 38 | Mouse TCAP 1 (41)<br><br>Gln Gln Leu Leu Gly Thr Gly Arg Val Gln Gly Tyr Asp Gly Tyr Phe<br><br>Val Leu Ser Val Glu Gln Tyr Leu Glu Leu Ser Asp Ser Ala Asn Asn<br><br>Ile His Phe Met Arg Gln Ser Glu Ile (SEQ. ID. NO. 1) |
| 70 | Human TCAP 1 (41)<br><br>Gln Gln Leu Leu Ser Thr Gly Arg Val Gln Gly Tyr Asp Gly Tyr Phe<br><br>Val Leu Ser Val Glu Gln Tyr Leu Glu Leu Ser Asp Ser Ala Asn Asn<br><br>Ile His Phe Met Arg Gln Ser Glu Ile (SEQ. ID. NO. 2) |
| 101 | G. Gallus TCAP-1 (41)<br><br>Gln Gln Leu Leu Asn Thr Gly Arg Val Gln Gly Tyr Asp Gly Tyr Phe<br><br>Val Leu Ser Val Glu Gln Tyr Leu Glu Leu Ser Asp Ser Ala Asn Asn<br><br>Ile His Phe Met Arg Gln Ser Glu Ile (SEQ. ID. NO. 3) |

Figure 1

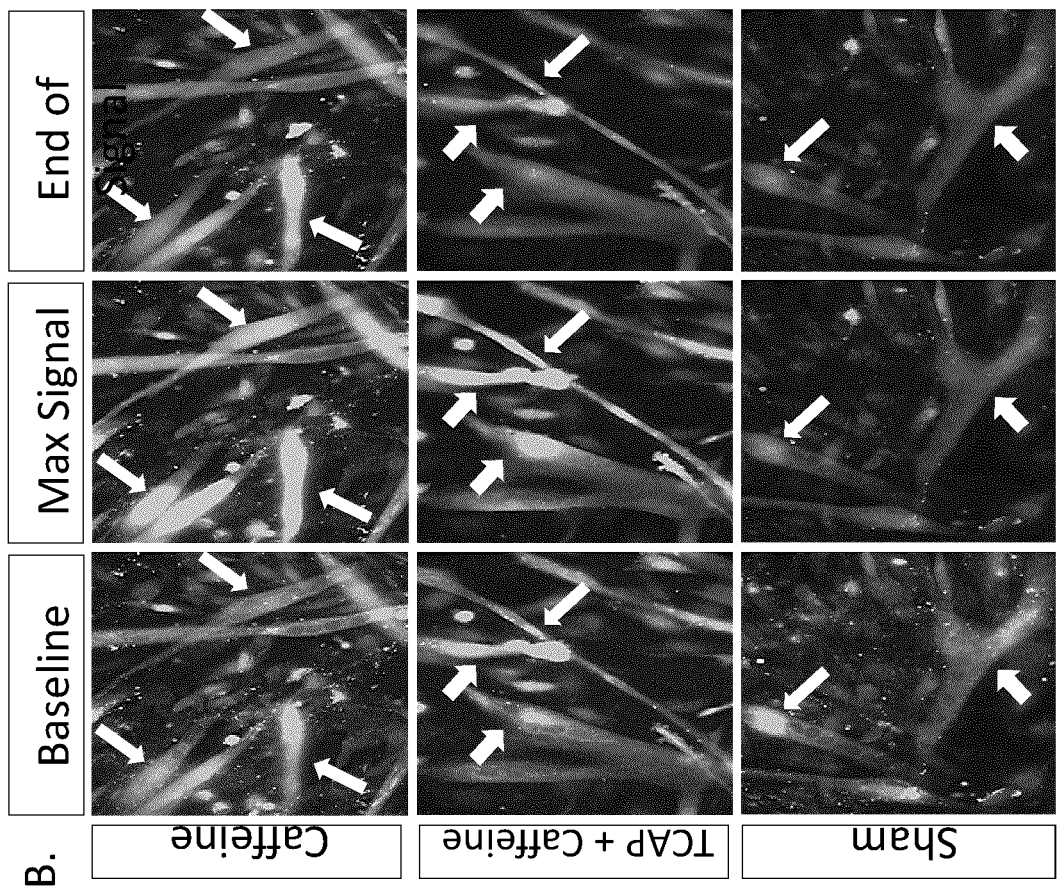
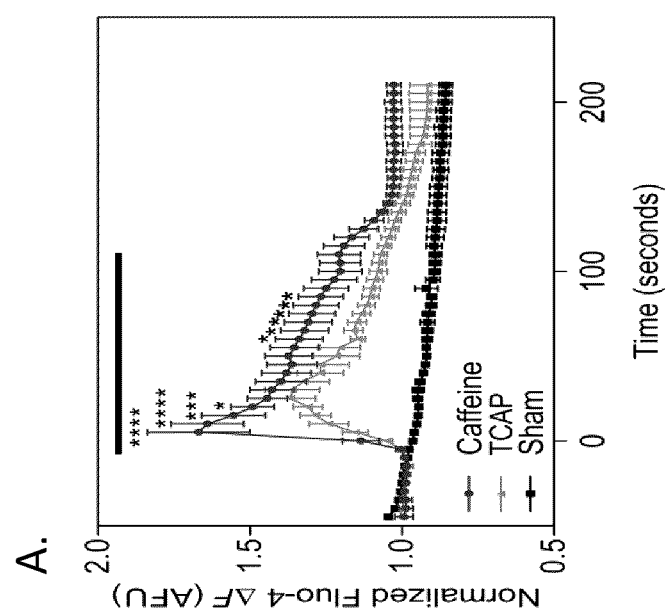
Figure 9

COMPOSITIONS, METHODS AND USES COMPRISING TENEURIN C-TERMINAL ASSOCIATED PEPTIDE -1 (TCAP-1) FOR ENHANCING MUSCLE PERFORMANCE

FIELD

The present invention relates to compositions, methods and uses of Teneurin C-Terminal Associated Peptide-1 (TCAP-1) to enhance muscle (e.g. skeletal muscle) function. In some embodiments the invention provides compositions, methods and uses for enhancing muscle recovery during or after fatigue. In some embodiments the invention provides compositions, methods and uses for restoring muscle function.

BACKGROUND

Muscle function and metabolism are intrinsically linked as evidenced by having metabolic syndromes resulting in poor muscle function or even its degradation. Muscle is one of the most important sites of glucose metabolism considering it is responsible for 40% of glucose-associated energy requirements (Richter & Hargreaves, 2013), and responsible for 80% of glucose disposal under insulin-stimulated conditions (Santos et al., 2008). Glucose provides the energy muscle contractions require by producing ATP via either anaerobic or aerobic pathways. Muscle contractions convert chemical energy into mechanical energy, a process resulting in excitation-contraction (EC) coupling. However, during prolonged muscle stimulation, such as exercise, this process can become uncoupled resulting in aberrant glucose and calcium regulation which may ultimately lead to decreased force production, known as fatigue. Aberrant glucose regulation is attributed to the fact that the rate of glucose uptake in the muscle is determined by the exercise intensity and duration (Richter & Hargreaves, 2013). With respect to calcium, the cycling between the sarcoplasmic reticulum and sarcomeres becomes inefficient and leads to poor contraction strength and velocity (Allen et al., 2008; Bellinger et al., 2008).

There is a need for a method to enhance and/or restore muscle function, particularly skeletal muscle function.

SUMMARY

The present invention provides a teneurin c-terminal associated peptide-1 (TCAP-1 peptide) and compositions comprising same for methods and uses for enhancing muscle function, in some embodiments more particularly to enhance skeletal muscle function. In some embodiments enhancing muscle function is restoring muscle function. In some embodiments the methods and uses for enhancing muscle function, such as skeletal muscle function, comprises: to increase force of contractions and/or to enhance (or shorten) muscle recovery times, for instance in situations of use or fatigue, and/or to restore muscle function.

In some embodiments, the invention provides a method for enhancing muscle function, in some embodiments to restore muscle function, particularly skeletal muscle function, comprising administering to a patient or subject in need thereof a therapeutically effective amount of a teneurin c-terminal associated peptide-1 (TCAP-1 peptide), or a pharmaceutically acceptable salt or ester thereof or a pharmaceutical composition comprising same, wherein the amino acid sequence of said TCAP-1 peptide consists essentially of:

(i) an amino acid sequence having at least 95% identity to an amino acid sequence selected from the group consisting of SEQ ID NOs: 1, 2 or 3 or a species homolog thereof;

optionally wherein:
(a) the carboxy terminal end of said TCAP peptide is amidated or comprises an amidation signal sequence; and/or
(b) when the amino terminal amino acid of said TCAP peptide is glutamine, it is in some embodiments in the form of pyroglutamic acid.

In some other embodiments, the invention provides a method for treating a skeletal muscle or muscle metabolic disorder by administration of a therapeutically effective amount of a TCAP-1 or a pharmaceutical composition comprising TCAP-1, as TCAP-1 is described herein to a patient or subject.

In some embodiments, TCAP-1 and compositions comprising same, can be used to enhance contractile performance and/or calcium cycling in skeletal muscle cells (e.g., myocytes) and tissues.

In a third aspect, the present invention provides TCAP-1 or compositions comprising same for the therapeutic use in treating or preventing disorders associated with muscular malfunction, wherein preferably the disorder is a skeletal muscle disorder, wherein preferably the muscular malfunction is associated with defective calcium cycling and/or defective contractile performance in muscle cells. Preferably, the TCAP-1 peptide is for enhancing and/or restoring calcium cycling and/or for enhancing and/or restoring contractile performance in muscle cells, such as skeletal muscle. In some embodiments, the skeletal muscle disorder may be selected from the group consisting of, muscle weakness, and muscular atrophy. In some embodiments, the invention provides compositions, methods and uses to facilitate rehabilitation to enhance and/or restore skeletal muscle function.

In some embodiments, the methods of the invention comprise reducing muscle recovery time during or after muscle stimulation, such as exercise or fatigue by using or administering an effective amount TCAP-1 or a pharmaceutical composition comprising same.

In some embodiments the patient or subject is a mammal, In some other embodiments, the mammal is selected from the group consisting of humans, dogs, cats, horses, sheep and cattle. In some embodiments the patient or subject is human.

Additional aspects and advantages of the present invention will be apparent in view of the description which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In order that the subject matter may be readily understood, embodiments are illustrated by way of examples in the accompanying drawings, in which:

FIG. 1 is the TCAP-1 SEQ. ID. Nos. 1-3 for mouse, human and *G. Gallus*, respectively.

FIG. 9: TCAP-1 modulates calcium cycling in C2C12 myotubes. C2C12 cells were differentiated until Day 6 myotubules and were loaded with fluo-4-AM ester dye (10 uM) which determines changes in cytosolic calcium levels by relative changes in fluorescence. Caffeine was administered as a stimulant for calcium release into the cytosol (black circle) to detect if TCAP-1 can modulate calcium cycling. C2C12 myotubes were either treated with caffeine alone, or pre-treated with TCAP-1 (100 nM) for 1 hour and subsequently stimulated with caffeine (gray triangle). Cells that were pre-treated with TCAP-1 significantly decreased peak caffeine-induced calcium release, as well as returned to baseline calcium levels significantly faster than caffeine treated alone at the end of experiment [n=4, 6-7 ROIs per coverslip; 2-way ANOVA, Tukey's post-hoc test, where *p<0.05, p<0.01, *p<0.001, **p<0.0001]. Sham treatment (black square) is a negative control to show unstimulated conditions (no caffeine) of cytosolic calcium levels. Quantified in (A), representative images of C2C12 myotubules with fluo-4 under experiment treatments shown in (B)

DETAILED DESCRIPTION

Figure 2:
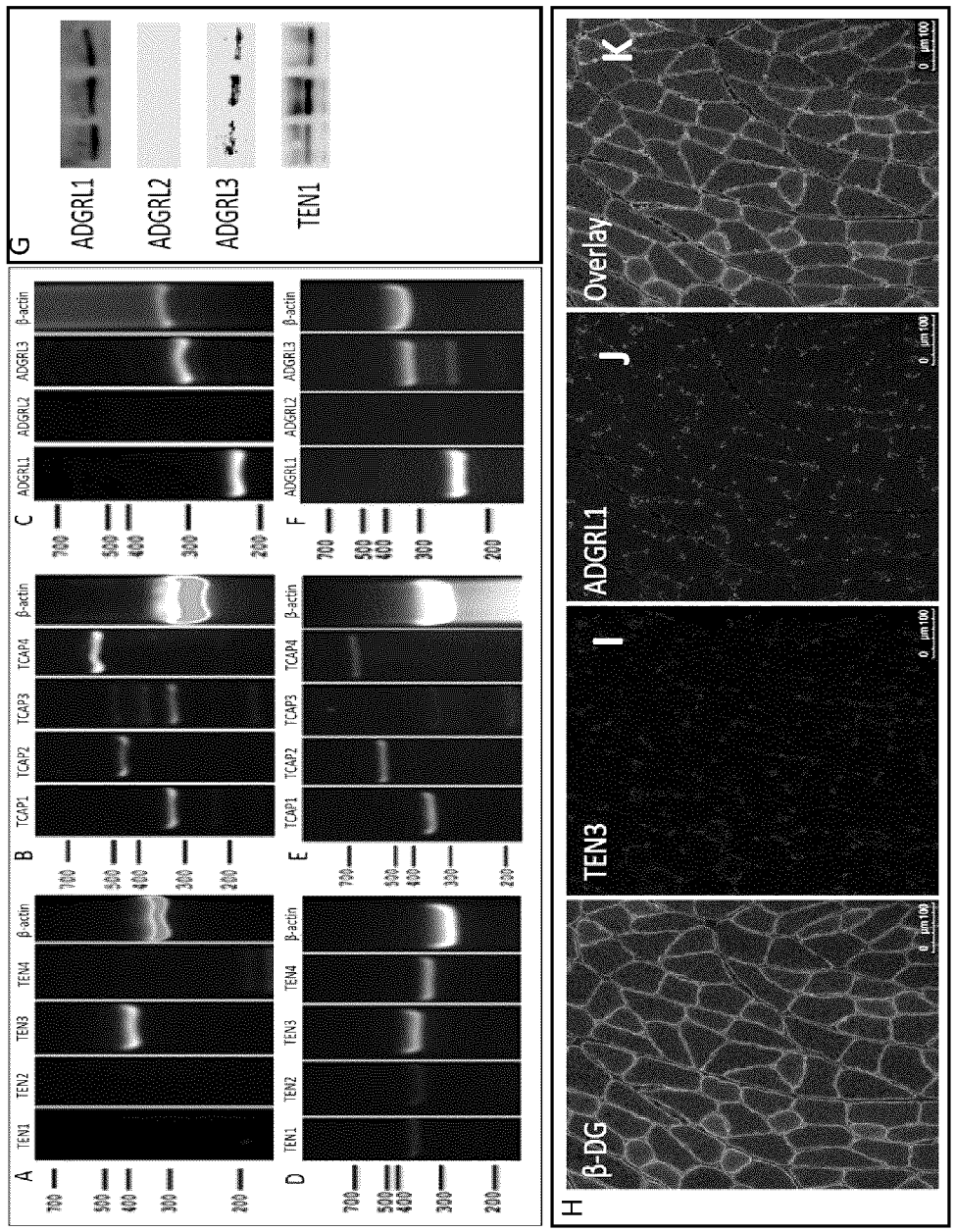
FIG. 2: Skeletal muscle contains the molecular components required for the teneurin/TCAP-ADGRL interaction. RT-PCR mRNA expression analyses of murine C2C12 skeletal muscle cells (A-C) and mouse hind limb muscle extract (D-F) were performed for all four teneurin, four TCAP and three ADGRL isoforms. β-actin was used as positive control. mRNA expression shows skeletal muscle both in vitro and in vivo expresses teneurins, TCAPs and ADGRLs. Western blot analyses of C2C12 cell lysates corroborate these findings at the protein level (G). Non-permeabilized rat tibialis anterior muscle sections demonstrate β-dystroglycan (β-DG) (H), teneurin-3 (TEN3) (I) and ADGRL1 (J) show strong co-localization of this complex in muscle. Overlay is shown (K)

Teneurin C-terminal associated peptides (TCAPs 1-4) are four paralogous bioactive peptides located at the distal extracellular end of each teneurin transmembrane protein. First described by Lovejoy et al and described in U.S. Pat. No. 8,088,889, which is herein incorporated by reference. TCAP-1 can be independently transcribed and has biological actions distinct from the teneurins, demonstrating functional independence from its proprotein. ADGRL (Latrophilin), an adhesion G protein-coupled receptor (GPCR), has recently been identified as part of the ligand-receptor complex that binds the teneurin/TCAP system. Previously elucidated in neurons, the teneurin/TCAP-ADGRL complex is associated with glucose metabolism; however, it is not well understood in other tissues.

Herein the present invention provides the first evidence of this ligand receptor system in skeletal muscle using RT-PCR and immunohistochemistry. As skeletal muscle is a major target of glucose uptake, the role of TCAP-1 with respect to energy metabolism was investigated both in vitro and in vivo. In vitro, 3H-2-deoxyglucose (2DG) uptake was assessed in an immortalized murine skeletal cell line (C2C12) after TCAP-1 administration and found a significant uptake in 2DG after 30 min. Similarly, in vivo, a significant uptake of 18F-2-deoxyglucose was observed as determined by functional positron emission tomography (fPET) in rats, which translates to increased muscle function. TCAP-1 treatment significantly increased muscle contractile force and prolonged contraction velocity and relaxation rate during fatigue, indicating an enhanced muscle function. Histological analyses of these muscles indicate that TCAP-1 treatment increases oxidative capacity as observed by significant increases in NADH levels. Further, it has been shown that TCAP-1 modulates calcium cycling, where it mediates calcium influx into the mitochondria resulting in mitochondrial depolarization. These actions have been established to increase mitochondrial activation, thereby increasing energy production in the cells. Thus, these novel findings demonstrate the teneurin/TCAP-ADGRL complex is expressed in skeletal muscle, and plays a major functional role in energy metabolism of the muscle.

Definitions

"C2C12" is an immortalized mouse myoblast cell line. The C2C12 cell line is a subclone of myoblasts that were originally obtained by Yaffe and Saxel at the Weizmann Institute of Science in Israel in 1977 [Yaffe, David; Saxel, Ora (1977-12-22). "Serial passaging and differentiation of myogenic cells isolated from dystrophic mouse muscle" (PDF). Nature. 270 (5639): 725-727. ISSN 0028-0836. doi:10.1038/270725a0]. C2C12 cells have also been isolated from rat lines. Developed for in vitro studies of myoblasts isolated from the complex interactions of in vivo conditions, C2C12 cells have gained significant utility in the biomedical research. These cells are capable of rapid proliferation and differentiation into myoblasts under high serum conditions. Mononucleated myoblasts can later fuse to form multinucleated myotubes under low serum conditions or starvation, the precursors to contractile skeletal muscle cells in the process of myogenesis.

"Muscle" in the context of the present invention means striated muscle tissue or muscle cells derived from striated muscle tissue and more specifically skeletal muscle cells/tissue.

"Muscle Function" as used in the context of the present invention means striated, more specifically skeletal muscle function and the ability of said muscle to contract and/or produce force. "Increased" or "Enhanced Muscle Function" as used herein means an enhancement and/or restoring of at least one aspect or component of muscle function, such as, shorter recovery time under muscle fatigue conditions, delayed onset of muscle fatigue, longer ability for muscle to sustain contraction or produce force, increased muscle contractile force, prolonged contraction velocity and relaxation rate during fatigue, increased oxidative capacity, and more efficient calcium handling/cycling, preferably the sarcoplasmic reticulum calcium handling/cycling or the uptake of calcium by the mitochondria. It would also include "restoring muscle function".

For example, since it is assumed that proper muscle function is tightly dependent on a functioning calcium handling within the muscle cell, the term "muscle function enhancing amino acid sequence or peptide" also refers to an amino acid sequence or peptide that is capable of enhancing and/or restoring the calcium handling/cycling, preferably the sarcoplasmic reticulum calcium handling/cycling in muscle cells, preferably skeletal muscle cells or the mitochondrial uptake of calcium.

The term "enhancing" in the context of the present invention, e.g., enhancing muscle function, contractile performance, and/or calcium handling, means that the particular function is increased/enhanced independently of whether the function is normal or defective, i.e., the muscle cell is healthy or diseased. In one embodiment the control setting is the muscle function, contractile performance, and/or calcium handling of the patient themselves compared to baseline or in some other embodiments a healthy patient or the average of a group of healthy patients. In some embodiments enhanced over baseline or control is at least 5%, 10%, 15%, 20%, 25%, 30%, 35%, 40% or more or any intervening percentage to said percentages (e.g., 6%, 18%, and so on). The term "restoring" in the context of the present invention, e.g., restoring muscle function, contractile performance, and/or calcium handling, preferably means that a defective or reduced function is brought back to closer to a normal or baseline function. In some embodiments, it could be a patient's own baseline or normal function (a state at which the patient was previously before the loss or reduction in function) or, in some embodiments, it could be as compared to a group of healthy or normal muscle functioning patients. In some embodiments it is at least 5%, 10%, 15%, 20%, 25%, 30%, 35%, 40%, 50% or more or any intervening percentage to said percentages (e.g., 6%, 18%, and so on) of the control function. In some embodiments it is to at least 50% of the normal function. "Normal muscle functioning patients" means an average value of the function exhibited by muscle cells derived from an individual who does not suffer from any muscle diseases or injuries.

The term "enhancing and/or restoring calcium cycling" in the context of the present invention means that either calcium cycling in myocytes, preferably sarcoplasmic reticulum calcium cycling, is improved under normal/non-pathological conditions or restored to normal or a desired function. According to the present invention the calcium cycling can preferably be enhanced or restored by improving e.g., increasing sarcoplasmic reticulum calcium content, increasing release of calcium from the sarcoplasmic reticulum during excitation-contraction coupling, reducing calcium leakage from the sarcoplasmic reticulum in quiescent muscle cells, reducing calcium spark frequency, and/or improving calcium uptake or re-uptake into the sarcoplasmic reticulum or the mitochondria. Without being bound to this theory, it is assumed that defective calcium cycling is one of the major reasons for defective contractile performance, e.g., contractile dysfunction, of muscle cells and a contributor to fatigue. Thus, it is assumed that enhancing or restoring calcium cycling also enhances and/or restores contractile performance and can help to delay fatigue onset or in recovery after fatigue.

In the context of the present invention, the term "contractile performance" encompasses any function that is associated with muscle contraction, for example, the force of muscle contraction or the timing of muscle contraction.

There are various methods of measuring contractile performance known in the art. In case of skeletal muscle tetanic contractions fall also within the term "contractile performance". "Defective contractile performance" refers to contractile dysfunction when compared to average values for normal/healthy muscle cells or tissue. For example, the contractile performance of a muscle cell or tissue is considered defective if, for example, the force of contraction of a given muscle cell or tissue deviates from the average value for normal/healthy muscle cells or tissue by at least 10%, preferably at least 20%, preferably at least 30%, more preferably at least 40%, and most preferably at least 50%, wherein the term "deviate" can refer to values less than the normal average value or to values higher than the normal average value, preferably it refers to values less than the normal average value. Preferably, the term "enhancing and/or restoring contractile performance" means the increase of contractile force of muscle cells or tissue, preferably skeletal muscle cells, as well as the correction of defective timing of muscle cell contractions. In this context, the term "defective timing" refers to inappropriately timed muscle contraction events such as tremor or twitching of skeletal muscle tissue.

"Muscle Fatigue" as herein means skeletal muscle's decline in ability to generate force.

"Therapeutically Effective Amount" as used herein when applied to dose or amount refers to that quantity of a compound or pharmaceutical composition that is sufficient to result in a desired activity upon administration to a living animal body. It is understood that a therapeutic amount may vary depending on a number of factors, including but not limited to gender, weight, body mass or body surface area, severity of a condition, age (e.g., child, teen, adult, or senior).

Description

Although TCAP and teneurins have been largely studied in the brain, their roles in skeletal muscle have not been studied. Skeletal muscle is one of the most important factors in determining the overall metabolism of an organism (Zurlo et al., 1990), which led to question if TCAP-1 has effects on muscle metabolism. Moreover, the recent elucidation of a putative receptor for teneurins and TCAPs have provided a new understanding of the teneurin/TCAP action on cells. Teneurin-2 and ADGRL1 have been shown to bind in the brain and have roles together in synaptogenesis (Boucard et al., 2014; Silva et al., 2011). This complex, involving multiple scaffolding proteins for maintaining integrity (reviewed in Woelfle et al., 2015), has not yet been investigated in skeletal muscle. Thus, it is of interest to investigate whether this complex exists in muscle and the roles it plays in this tissue, given the major role that vertebrate skeletal muscle plays with respect to glucose metabolism.

Therefore, the inventors examined the specific role of TCAP-1 in skeletal muscle metabolism and established the expression of the teneurin/TCAP-ADGRL ligand-receptor complex in skeletal muscle and that it plays a major role in glucose uptake; increased aerobic metabolism and increased or enhanced muscle function.

Teneurin C-Terminal Associated Peptide-1 (TCAP-1)

TCAP-1 as used herein is a peptide that consists of a sequence found at the c-terminal of Teneurin M-1 peptide, more particularly described below. There is considerable cross-species homology.

In some embodiments the TCAP-1 peptide ("TCAP-1") is a 41-mer peptide selected from SEQ. ID. NOs 1 to 3 (see also FIG. 1). In some embodiments it is an amidated peptide, (such as a C-terminal amidated peptide), in some other embodiments the TCAP has a pyroglutamic acid at the N-terminal. In other embodiments, it has both a pyroglutamic acid at the N-terminal and is amidated at the C-terminal.

In other embodiments it is a human TCAP-1. In some embodiments it is a 41-mer c-terminal amidated peptide consisting of the following sequence:

```
Amidated Human TCAP-1 (41 mer)
Gln* Gln Leu Leu Ser Thr Gly Arg Val Gln Gly Tyr Asp Gly Tyr Phe Val Leu Ser Val Glu Gln Tyr Leu Glu Leu Ser Asp Ser Ala Asn Asn Ile His Phe Met Arg Gln Ser Glu Ile-NH₂
*In some embodiments the N-terminal glutamic acid may be a
pyroglutamic acid.
```

In some other embodiments, the peptide used is a salt, ester, solvate, polymorph or enantiomers of SEQ. ID. NOs. 1 to 3, preferably SEQ. ID. NO. 1, or any amidated or pyroglutamic acid or amidated and pyroglutamic acid form of SEQ. ID. NOs. 1 to 3.

In some other embodiments, conservative substitutions or modifications can be made to the peptide sequence which does not affect its structure or function and thus could be used for the present invention, such as various species homologs. For instance those present in species homologs, such as the mouse, human or *G. gallus* TCAP-1 sequences (SEQ. ID. NOs. 1-3) where the fifth amino acid may be selected from: Gly, Asn or Ser. In some embodiments, the peptide has 95% identity to SEQ. ID. NOs. 1, 2, or 3.

Pharmaceutical Compositions

The present invention contemplates the administration of a pharmaceutical composition comprising TCAP-1 as described herein (including an amidated and/or pyroglutamic acid form of TCAP-1 or a peptide with 95% identity to SEQ. ID. NOs. 1-3) and a pharmaceutically acceptable carrier.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the Federal or a state government or listed in the U.S. Pharmacopeia (USP), National Formulary (NF), or other generally recognized pharmacopeia for use in mammals, and more particularly in humans. Active Pharmaceutical Ingredients (APIs) of the present invention may be in the form of pharmaceutically acceptable salts. "Pharmaceutically acceptable salts" refers to those salts which possess the biological effectiveness and properties of the parent compound and which are not biologically or otherwise undesirable.

The pharmaceutical compositions of the present invention may comprise one or more excipients. Excipients which may be used include carriers, surface active agents (surfactants), thickening (viscosity) agents, emulsifying agents, binding agents, dispersion or suspension agents, buffering agents, penetration-enhancing agents, solubilizers, colorants, sweeteners, flavoring agents, coatings, disintegrating agents, lubricants, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference.

The term "carrier" applied to pharmaceutical compositions of the invention refers to a diluent, excipient, or vehicle with which an active compound is administered. Such pharmaceutical carriers can be liquids, such as water, saline solutions, aqueous dextrose solutions, aqueous glycerol solutions, and lipids and oils, including those of petroleum, animal, vegetable or synthetic origin. Suitable pharmaceutical carriers are described in "Remington's Pharmaceutical Sciences" by E. W. Martin, 18.sup.th Edition.

In some embodiments, the dosage form is a subcutaneous dosage form. This differs from direct administration to the brain, amygdala, or Intracerebroventricular ("ICV"). Subcutaneous administration has many advantages over direct administration to the brain.

In some embodiments as in the composition used in the Examples, the composition dissolves an amidated and pyroglutamic acid form of TCAP in a saline solution and is subcutaneously administered into animals (not ICV or amygdala). This formulation has advantages over prior forms for delivery, i.e., ICV or amygdala, in that it does not require additional sedatives, or the like for administration.

The compositions may, if desired, be presented in a pack or dispenser device which may contain one or more unit dosage forms containing the active ingredient(s). The pack may, for example, comprise metal or plastic foil, such as a blister pack. Compositions of the invention formulated in a compatible pharmaceutical carrier may also be prepared, placed in an appropriate container, and labeled for treatment of an indicated condition.

In some embodiments, TCAP-1 and the pharmaceutical compositions of the invention are used to enhance and/or restore muscle function in an animal, in some embodiments mammals, including but not limited to humans, dogs, cats, horses, sheep, cattle. It is accepted in the literature that mammals have a common muscle structure. In particular it has been shown that rats and humans are similar in muscle fiber heterogeneity and thus results in rat studies for skeletal muscle are analogous to what would be occurring in human skeletal muscle (See Smerdu, V. et al, "Type IIx myosin heavy chain transcripts are expressed in type IIb fibers of human skeletal muscle" Am. Physiological Society 1994, pp. C1723-C1728).

Methods and Uses

In some embodiments TCAP-1 and the pharmaceutical compositions comprising same can enhance and/or restore muscle function and enhance muscle recovery during or after fatigue and/or overcome muscle fatigue.

In some embodiments the TCAP-1 and pharmaceutical compositions comprising same of the present invention can be used to enhance or restore contractile performance in skeletal muscle, such as one or more of the following: increased contractile force or longer ability for muscle to sustain contraction or produce force, prolonging contractile velocity and relaxation rate during and after fatigue, shortening muscle recovery times (e.g. during or after exercise or fatigue), delaying onset of fatigue, increasing oxidative capacity.

In some other embodiments, TCAP-1 and pharmaceutical compositions comprising same of the present invention can be used to enhance or restore calcium cycling or making calcium cycling more efficient. In some other embodiments TCAP-1 and the pharmaceutical compositions comprising same of the present invention can be used to enhance clearance of calcium from the cytosol or enhance calcium cycling through the cytosol or enhance calcium uptake by mitochondria.

In some embodiments, the TCAP-1 and pharmaceutical compositions comprising same of the present invention have many uses, including preventing or reducing muscle atrophy, muscle degradation or the like, for instance in instances when a patient is in hospital or bedridden (e.g. due to illness, accident, surgery or temporary or permanent disability or temporary or permanent paralysis), or not as mobile or is recovering or in the midst of rehabilitation of a skeletal muscle related disability, injury, or disorder. It can also be useful to enhance muscle function such as for physical training (involving skeletal muscle) for instance in cases of physical rehabilitation or to enhance fitness (e.g. ability to train or rehab more, longer, with less recovery time).

The present invention is described in the following Examples, which are set forth to aid in the understanding of the invention, and should not be construed to limit in any way the scope of the invention as defined in the claims which follow thereafter.

EXAMPLES

The following examples illustrate the role of TCAP-1 in skeletal muscle metabolism and function. It is herein established that the teneurin/TCAP-ADGRL ligand-receptor complex is expressed in skeletal muscle and that it plays a major role in glucose uptake. It is further shown that TCAP-1 administration increases aerobic metabolism and muscle function and that it can be used to enhance and/or restore muscle function.

Materials and Methods

TCAP-1 Composition

Amidated human TCAP-1 (SEQ. ID. NO. 1) was suspended in 0.9% saline. [10 nmol/Kg, Ambiopharm] for subcutaneous injection in the interscapular region.

Amidated human TCAP-1 peptide used in the composition was synthesized on an automated peptide synthesizer, Model Novayn Crystal (NovaBiochem) on PEG-PS resin using continuous flow Fmoc chemistry (Calbiochem-NovabiochemGroup). Eight times excess diisopropyl ethyl amine (Sigma-Aldrich) and four times excess Fmoc-amino acid activated with HATU (O-(7-azabenzotriazol)-1-3, 3-tetramethyluronium hexfluorophosphate; Applied Biosystems) at a 1:1 (mol/mol) ratio were used during the coupling reaction. The reaction time was 1 h. A solution of 20% piperidine (Sigma-Aldrich) in N, N-dimethylformide (DMF; Caledon Laboratories) was used for the deprotection step in the synthesis cycle. The DMF was purified in-house and used fresh each time as a solvent for the synthesis. The cleavage/deprotection of the final peptide was carried out with trifluoroacetic acid (TFA), thioanisole, 1, 2 ethandithiol, m-cresole, triisopropylsilane, and bromotrimethyl silane (Sigma-Aldrich) at a ratio of 0:10:5:1:1:5. Finally, it was desalted on a Sephadex G-10 column using aqueous 0.1% TFA solution and lyophilized.

Animals

All animal studies were performed in Canada and followed the requirements set out by the Canadian Council for Animal Care (CCAC) and were approved by the University Animal Care Committee (UACC).

Male adult Sprague-Dawley rats (~350 g) were used for the muscle function studies. Male adult Wistar rats (~250 g) were used for the functional positron emission tomography tests.

Cell Culture of C2C12 Cell Line

Immortalized murine skeletal cell line C2C12 cells were used for all in vitro studies. Cells were maintained at 60-70% confluency with Dulbecco's Modified Eagle Medium (DMEM) supplemented with 20% fetal bovine serum (FBS) and penicillin/streptomycin antibiotic combination. To induce differentiation, the media was changed to DMEM supplemented with 10% horse serum and penicillin/streptomycin antibiotic combination, and cells were allowed to differentiate for 6 days (media replaced every 24 h). For treatment, cells were serum starved for 3 h and then treated with either vehicle (ddH20) or TCAP-1 (100 nM).

Reverse Transcription (RT)—Polymerase Chain Reaction (PCR)

RNA was extracted from C2C12 cells using TRIzol (Thermo Scientific, Waltham, Mass., USA) using the manufacturer's instructions. Reverse transcription reactions contained 2 μL purified total RNA, 1 μl random primer Mix (Bio-Rad), 1 μL deoxynucleotide solution mix (New England Biolabs), and 8 μL water. Reactions were incubated in a Fisher Scientific Isotemp 125D Dry Bath Incubator for 5 min at 16° C. and then for 1 min at 4° C. Aliquots of 4 μL First Strand Buffer (Invitrogen), 2 μL 0.1 M DTT (Invitrogen), and 1 μL SuperScript II Reverse Transcriptase (Invitrogen) were added to the reaction mix. The 20 μL reactions were incubated for 10 min at 25° C., 50 min at 42° C., 15 min at 70° C., and then held at 4° C. The 29.5 μL PCR reaction mix included 5 μL cDNA, 2 μL Forward Primer and 2 μL Reverse Primer (Invitrogen), 14.2 μL water (Sigma), 3 μL 10×Taq Buffer with KCl (Thermo Scientific), 1.8 μL MgCl2 (Thermo Scientific), 1 μL Deoxynucleotide Solution Mix (New England Biolabs), and 0.5 μL Taq DNA Polymerase (Bioshop). The reactions were incubated in an Eppendorf Mastercycler Gradient Thermal Cycler for 7 min at 95° C.; followed by 35 cycles of 60 sec at 95° C., 90 sec at 65° C., and 35 sec at 72° C.; and then held at 4° C. DNA samples (14.4 μL) were then electrophoresed on a 6% agarose gel at 100 V for 1.5 hs. Gels were visualized using a Bio-Rad ChemiDoc MP System with 0.5 sec exposure. Band sizes as expected by primer pairs are as follows: teneurin-1 (402 bp), teneurin-2 (405 bp), teneurin-3 (427 bp), teneurin-4 (369 bp), TCAP-1 (351 bp), TCAP-2 (496 bp), TCAP-3 (506 bp), TCAP-4 (602 bp), ADGRL1 (249 bp), ADGRL2 (203 bp), ADGRL3 (327 bp), and β-actin (357 bp).

Western Blot

Following TCAP-1 treatments, C2C12 cells were lysed with 500 μL of RIPA buffer supplemented with PMSF. Cells were harvested and centrifuged at 14000 rpm for 20 min at 4° C. The pellet was discarded and supernatant aliquoted into two tubes, 30 μL for protein quantification and the remainder ~450 μL for western blot analysis, and stored in −20° C. A Pierce BCA protein assay (Thermo Fischer Scientific) was performed to quantify protein concentrations for standardizing dilutions of respective supernatant samples. Samples (15 μg) were re-suspended in sample buffer and size fractioned by SDS-PAGE (10%) at 100V for 1 h. Proteins were then electrotransferred to Hybond-ECL nitrocellulose membranes (Amersham) for 2 h at 100 V. Membranes were washed with phosphate buffer solution (PBS) and blocked in 5% milk-PBST (5% w/v non-fat milk powder in PBS with 0.2% Tween®20) at room temperature (RT) for 1 under agitation. Afterwards, membranes with incubated with rabbit primary antibodies in 1% milk-PBST overnight at 4° C. with gentle agitation. Following 24 h, the membranes were given 3×5-minute washes in fresh PBST at RT and incubated with anti-rabbit horseradish peroxidase (HRP)-conjugated secondary antibody (VWR, Amersham) diluted to 1:7500 in 1% milk-PBST for 1 h at RT with gentle agitation. The membranes underwent 3×5-min washes in fresh PBST at RT. Subsequently, proteins were detected by adding chemiluminescence detection reagent (ECL Amersham) to the membranes and exposing onto ECL Hyperfilm (VWR) for 10-60 min.

Immunohistofluorescence

The tibialis anterior (TA) muscle was excised from the Sprague-Dawley rats and flash-frozen in liquid nitrogen cooled-isopentane, where it was stored at −80° C. until use. Tissue was sectioned at 10 μm using a cryostat at −20° C. and put on coverslides. The sections were then fixed using ice-cold methanol. Sections were then blocked for 1 h using 10% normal goat serum (NGS). Primary antibody diluted in 1% NGS was then added and allowed to incubate overnight at 4° C. The following morning after PBS washes, the secondary antibody was added and allowed to incubate for 1 h at RT in the dark. Coverslips were then mounted and imaged using confocal microscopy (Leica TCS-SP8) at 400× magnification (scale bar, 100 μm). For fluorescence analyses of protein expression, Image J software was used to measure arbitrary fluorescent units (AFU), with increase of AFU representing increase in protein expression. An average of 8 measurements were taken per fiber to determine ADGRL1 level of expression (n=5).

Mouse Diacylglycerol (DAG) and Mouse Inositol Triphosphate (IP3) ELISA Assays

The protocols provided by commercial DAG and IP3 assays (MyBiosource, San Diego, Calif. USA). Briefly, immortalized mouse C2C12 cells were prepared using the TCAP-treatment protocol described previously. Cells were added to a microELISA plate coated with purified mouse DAG or IP3 antibodies, respectively. Subsequently, 3,3',5,5'-tetramethylbenzidine (TMB) solution was added to detect the HRP-conjugates as the colour changes. Finally, a sulphuric acid solution was added to terminate the reaction. The absorbance change was measured at a wavelength of 450 nm using a spectrophotometer (SpectraMax Plus).

Radioactive Glucose Uptake In Vitro

Immortalized murine skeletal C2C12 cells were allowed to proliferate and differentiate and glucose uptake protocol was followed as previously described with minor modifications (Maher et al., 1991; Uemura & Greenlee, 2006). At day 6 post-plating, cells were washed 2× with Locke's buffer (154 mM NaCl, 5.6 mM KCl, 2.3 mM $CaCl_2$, 3.6 mM $NaHCO_3$, 5 mM HEPES) without serum and glucose. The culture was incubated in the Locke's buffer for 1 h at 37° C. followed by exposure to 100 nM insulin, 100 nM TCAP-1, 100 nM SC-TCAP-1, or saline. 3H-2-deoxyglucose (0.5 μCi/ml) was added to culture 5 min before termination of treatment exposure. Uptake of 3H-2-deoxyglucose was stopped immediately after 5 min with 3× washes of ice-cold 0.9% NaCl solution. The cells were digested with 1 mL of 0.05 N NaOH at 0, 15, 30, 45, 60, 90 and 120 min after treatment. Cell lysates were used for determination of radioactivity by a beta liquid scintillation counter (Beckman Coulter).

Functional Positron Emission Tomography (fPET)

Functional Positron emission tomography (fPET) was performed using a Siemens Inveon microPET small animal PET scanner, and [18F]-2-deoxyglucose (FDG) radiotracer (IBA Molecular) and protocol was followed as previously described (Hogg et al., manuscript in review). PET scans were acquired on all of the animals 3 days post-dosing. The animals were injected intravenously with approximately 1 mCi of FDG. The FDG uptake occurred under anesthesia for 90 min. Body temperature was maintained with a thermostat-regulated recirculating water heated pad. Static emission data was acquired for 20 minutes. The PET list mode data was converted to 2-dimensional (2D) sinograms, corrected for random coincidences, and normalized for scanner uniformity. PET image analysis was performed using the Amira 5.5.0 analysis software package. For whole body ROIs, a low threshold was set to delineate specific signals in the whole body while eliminating background. The total PET counts were calculated from all voxels within the segmented volumes of interest. (Percent injected dose (% ID)) was calculated by normalizing the total counts in each tissue of interest at each time point, to the whole body total counts calculated over 1 min from the whole body max uptake time point, for each animal, during the first 90 min post FDG administration.) These images were then compiled into 3D projections, thus allowing for accurate analyses of muscle tissue. Fluorescence of the mean pixel was calibrated to volume of muscle being analyzed (mean pixel fluorescence/mm3).

Electrical Muscle Stimulation

Electrical muscle stimulation protocol was followed as described by Holwerda and Locke (2014) with minor modifications. Briefly, sixteen male adult Sprague-Dawley rats (250 g) were allowed to acclimate for 1 week on a 12:12 LD cycle. For 5 days daily, half of the rats (n=8) were treated with physiological saline control, and the other half (n=8) was treated with mouse-TCAP-1 (10 nmoles/kg) by subcutaneous injection in the interscapular region. Three days from the last treatment, animals were anesthetized with 5% isofluorane in 1 L/min $O_2$, and subsequently positioned into testing apparatus. A 25 g needle was inserted through the soft tissue of the knee in order to ensure a stable position. The foot was placed on the lever attached to a servomotor and taped in position. Electrodes were placed below the skin but adjacent to the tibialis anterior (TA) muscle. The correct voltages for peak tetanic tension was established by increasing voltage by 1 volt increments. The test began with a single tetanus and single twitch protocol to establish baseline. The 6-min fatigue protocol (8V, 200 Hz, 300 ms) was started. Immediately following the termination of the protocol, tetanic and twitch tensions were recorded at 0, 1, and 5 mins. Animals were immediately sacrificed after recovery measurements were recorded.

Oxidative Capacity Studies—NADH Staining

Tibialis anterior muscles from the treated Sprague-Dawley rats were flash-frozen in liquid-nitrogen-cooled isopentane until cryosectioned at 10 µm thickness. Cryosections were then washed 2× with PBS, and then 0.2% NBT solution in PBS containing 0.1% NADH was added and allowed to incubate for 30 min at 37° C. Slides were washed 2× in PBS before mounted with cryoseal and imaged with Canon camera and Leica bright-field microscope at 100× magnification. Images were analyzed on Image J software and frequency distribution curves were constructed, where the darker the pixel represents higher NADH levels. Frequency curves were built based on average of five pictures per tissue, with a minimum of three tissues analysed for each group.

Calcium Imaging in Live C2C12 Cells

For live-cell fluorescence experiments, immortalized murine C2C12 skeletal muscle cells were grown and fully differentiated on Poly-D-lysine coated 25 mm round No. 1 glass coverslips (Warner Instruments, Hamden, Conn., USA). Cells were grown in Dulbecco's Modified Eagle Medium (DMEM) supplemented with 20% fetal bovine serum (FBS), 100 U/ml penicillin and 100 µg/ml streptomycin (Invitrogen, Burlington, ON, Canada), and stimulated differentiation with DMEM supplemented with 10% horse serum (HS), 100 U/ml penicillin and 100 µg/ml streptomycin (Invitrogen, Burlington, ON, Canada. Changes in intracellular calcium were assessed using the membrane-permeable calcium sensitive fluorescent indicator fluo-4, AM (Invitrogen, Burlington, ON, Canada). Cells were loaded with fluo-4 by incubating a single coverslip in DMEM containing 10 µM fluo-4 (from a 1 mM stock solution in DMSO) for 30 min (37° C.) followed by a 15 min wash in Locke's Buffer containing (in mM): 154 mM NaCl, 4 mM $NaHCO_3$, 5 mM KCl, 2.3 mM $CaCl_2$, 1 mM $MgCl_2$, 5 mM glucose and 10 mM Hepes (pH 7.4); osmolarity 305-310 mOsmol at 22° C. During loading, the acetate groups on fluo-4 are removed by intracellular esterases reducing dye leakage. In experiments assessing changes in intracellular calcium, coverslips were placed in a flow-through bath chamber (RC-40HP, Warner Instruments, Hamden, Conn., USA) of an inverted microscope (Axio Observer Z1, Zeiss, Toronto, ON, Canada) equipped with a 40× oil immersion objective. Cells were continuously bulk perfused with Locke's buffer via a gravity drip perfusion system at a rate of 2-3 ml min-1 and experiments were conducted at a room temperature (RT) of 22° C. Changes in fluo-4 fluorescence was imaged using a green fluorescent protein (GFP) filter set (Semrock, Rochester, N.Y., USA) and a X-Cite 120 fluorescence illumination system (Excelitas Technologies, Mississauga, ON, Canada), controlled by Volocity 4.0 imaging software (Quorum Technologies Inc., Guelph, ON, Canada). Fluorescence emissions were detected with an Orca-ER Hamamatsu B/W CCD digital camera (Hamamatsu, Middlesex, N.J., USA). Fluo-4 was excited with a wavelength of 480 nm for 100 ms every 5 sec and fluorescence emission was measured at wavelength of 516 nm. Caffeine (4 mM; Sigma Aldrich, Oakville, ON) was applied to C2C12 myotubes to stimulate calcium release from the sarcoplasmic reticulum. Cells were either pre-treated with TCAP-1 (100 nM) for 1 hour before stimulation with caffeine. Using velocity 4.0 imaging software, multiple regions of interests (ROIs) were taken from each coverslip to be analysed.

Measuring Mitochondrial Membrane Potential in C2C12 Cells with Rhodamine-123.

C2C12 myotubes were cultured as previously described above. Changes in mitochondrial membrane potential were assessed using fluorescent indicator Rhodamine123 (R123). Cells were loaded with R123 by incubating a single coverslip in DMEM containing 5 µM R123 (from a 1 mM stock solution in DMSO) for 30 min (37° C.) followed by a 15 min wash in Locke's Buffer containing (in mM): 154 mM NaCl, 4 mM $NaHCO_3$, 5 mM KCl, 2.3 mM $CaCl_2$, 1 mM $MgCl_2$, 5 mM glucose and 10 mM Hepes (pH 7.4); osmolarity 305-310 mOsmol at 22° C. In experiments assessing changes in mitochondrial membrane potential, coverslips were placed in a flow-through bath chamber (RC-40HP, Warner Instruments, Hamden, Conn., USA) of an inverted microscope (Axio Observer Z1, Zeiss, Toronto, ON, Canada) equipped with a 40× oil immersion objective. Cells were continuously bulk perfused with Locke's buffer via a gravity drip perfusion system at a rate of 2-3 ml min-1 and experiments were conducted at a room temperature (RT) of 22° C. Changes in R123 fluorescence was imaged using a green fluorescent protein (GFP) filter set (Semrock, Rochester, N.Y., USA) and a X-Cite 120 fluorescence illumination system (Excelitas Technologies, Mississauga, ON, Canada), controlled by Volocity 4.0 imaging software (Quorum Technologies Inc., Guelph, ON, Canada). Fluorescence emissions were detected with an Orca-ER Hamamatsu B/W CCD digital camera (Hamamatsu, Middlesex, N.J., USA). R123 was excited with a wavelength of 480 nm for 100 ms every 5 sec and fluorescence emission was measured at wavelength of 516 nm. Caffeine (4 mM; Sigma Aldrich, Oakville, ON) was applied to C2C12 myotubes to stimulate calcium release from the sarcoplasmic reticulum. Cells were either pre-treated with TCAP-1 (100 nM) for 1 hour before stimulation with caffeine. Using velocity 4.0 imaging software, multiple regions of interests (ROIs) were taken from each coverslip to be analysed.

Statistics

Tests were used to assess statistical significances. Student's t-test and ANOVAs were used unless specifically stated otherwise. Statistics were denoted by $*p<0.05$, $p<0.01$, $*p<0.001$, $****p<0.0001$.

Example 1: Expression of the Teneurin/TCAP ADGRL Complex in Rat Skeletal Muscle and C2C12 Cells (a) Comparison Between In Vivo and In Vitro Expression; Skeletal Muscle Expresses Teneurins, TCAPs, and ADGRLs.

In order to determine genetic expression of the molecular components associated with the teneurin/TCAP-ADGRL complex, reverse transcription (RT)-PCR analyses using RNA extracts from both C2C12 murine skeletal cells and mouse hind limb muscle were used for all of the four teneurin, four TCAP, and three ADGRL isoforms. In the C2C12 cells, of the four teneurins, only teneurin-3 was expressed, whereas all four of the TCAP peptides were expressed. ADGRL1 and ADGRL3 were both expressed, but no expression of ADGRL2 was observed (FIG. 2A-C). Mouse hind limb skeletal muscle extracted and homogenized showed similar expression to the in vitro cell line. It showed high expression of teneurin-3 as well as teneurin-4, but showed low expression of teneurin-1 and teneurin-2. Similar to cell line results, the muscle extract showed expression of all of the four TCAP peptides as well as ADGRL1 and ADGRL3, with no expression of ADGRL2 (FIG. 2 D-F). Moreover, protein level expression shown by western blot analyses of C2C12 cell lysates corroborated the genetic expression pattern established by RT-PCR (FIG. 2 G). After establishing that the necessary molecular components were expressed in vitro and in vivo, we next aimed to assess if these proteins were localized together to demonstrate they could potentially form the teneurin/TCAP-ADGRL complex (reviewed in Woelfle et al., 2015). Immunohistochemistry on non-permeabilized rat tibialis anterior muscle sections was used to visualize teneurin-3 (FIG. 2 I, Ten-3), ADGRL1 (FIG. 2 J, ADGRL1), and β-dystroglycan (FIG. 2 H, β-DG), at the plasma membrane. There was strong co-localization of all three proteins (FIG. 2 K, Overlay), consistent with previous literature of this complex observed in different tissues (Boucard et al., 2014; Chand et al., 2012; Chand et al., 2014.)

(b) Defining the C2C12 System with Respect to Teneurins/TCAP.

Regulation of Downstream ADGRL1 Signaling, DAG and IP3 Levels.

Figure 3:
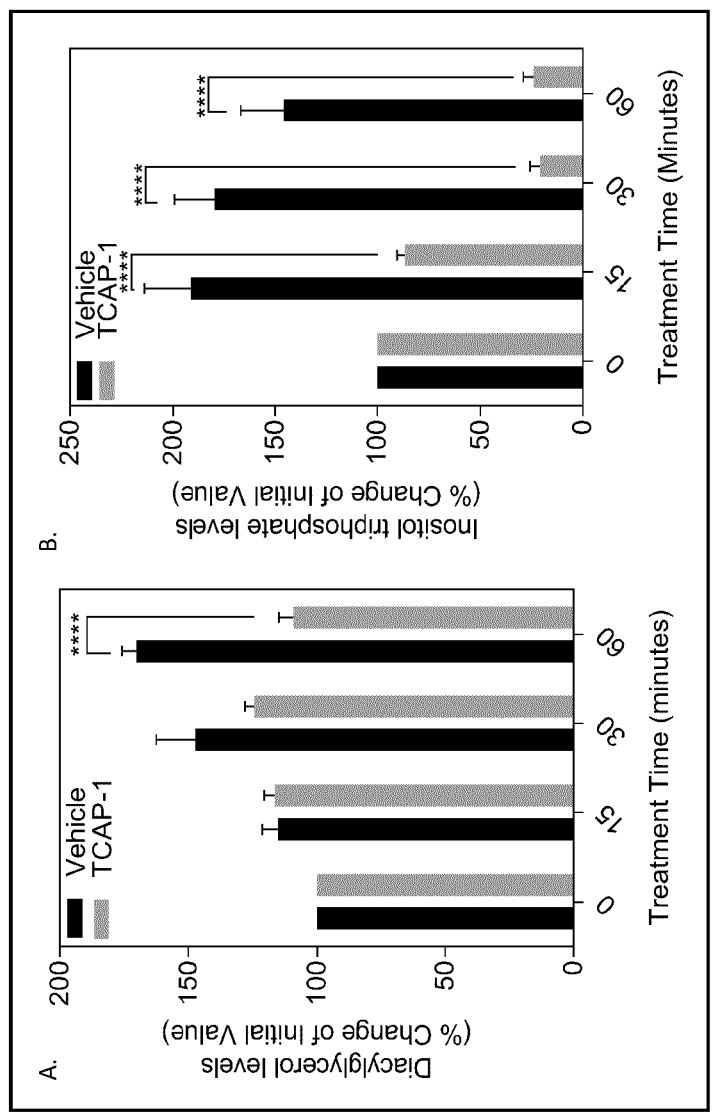
FIG. 3: TCAP-1 significantly reduces diacylglycerol (DAG) and inositol triphosphate (IP3) levels in C2C12 skeletal cell line. Enzyme-linked immunosorbent assays were used to determine levels of DAG and IP3 in C2C12 cell lysates after various time treatments to investigate downstream signaling of ADGRL1 by TCAP-1. TCAP-1 significantly reduces DAG levels after 60 mins (A) and significantly reduces IP3 levels after 15 minutes, minutes (n=6; two-way ANOVAs,*p<0.05, p<0.01, *p<0.001, ****p<0.0001) (B)

ADGRL downstream signaling has been associated with phospholipase C (PLC)-inositol triphosphate (IP3)/diacylglycerol (DAG) pathway as shown by stimulation with its exogenous ligand, α-latrotoxin (Davletov et al., 1998; Rahman et al., 1999), thus the effect of TCAP-1 on these downstream molecular signals in the C2C12 skeletal cell model were investigated. Analyses revealed that after 60 minutes of TCAP-1 (100 nM) treatment, DAG levels significantly decreased (p<0.0001) compared to vehicle treatment (FIG. 3 A). Similar, IP3 levels were also significantly reduced after 15 minutes (p<0.0001) after TCAP-1 (100 nM) treatment (FIG. 3 B). These results indicate TCAP-1 is significantly affecting downstream signaling of ADGRL1, thereby corroborating the functionality of the teneurin/TCAP-ADGRL complex in skeletal muscle.

Example 2: Glucose Action in C2C12 Cells In Vitro

Figure 4:
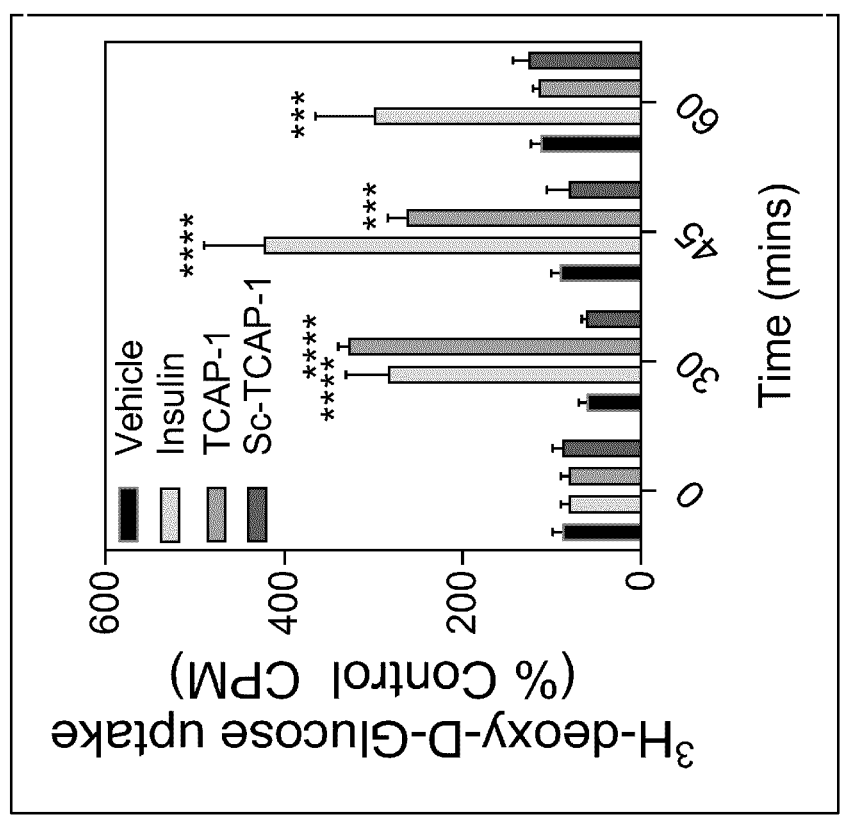
FIG. 4: TCAP-1 significantly increases glucose uptake in C2C12 murine skeletal muscle cells in vitro. TCAP-1 treatment to immortalized C2C12 skeletal muscle cells significantly increased 3H-deoxy-D-glucose uptake at 30 and 45 minutes compared to vehicle treatment (n=3; two-way ANOVA, ****p<0.0001), peaking at 300% increase at 30 minutes. Insulin and scrambled-TCAP (sc-TCAP-1) peptide were used as a positive and negative control, respectively.

Glucose uptake was investigated in vitro to investigate TCAP-1 actions in muscle, as this action has been well established in neurons (Hogg et al., manuscript in review). First, radioactively-labeled deoxy-D-glucose ($^3$H-DG) was added to C2C12 cells and its uptake was measured to determine glucose uptake into the cells with either vehicle (ddH$_2$O), TCAP-1 (100 nM), insulin (100 nM) or scrambled-TCAP-1 (100 nM) treatment, with the last two treatments used as a positive and negative control, respectively. Deoxyglucose cannot be further metabolized in the glycolysis pathway once it enters the cell, thus represents a better representation of glucose uptake. TCAP-1 treatment significantly increased $^3$H-DG uptake into C2C12 cells at 30 and 45 (p<0.0001, p<0.001, respectively), with over 300% more glucose uptake than vehicle treatment at 30 minutes (FIG. 4). TCAP-1 treatment was similar to insulin-stimulated glucose uptake at 30 minutes, and scrambled-TCAP-1 did not induce any glucose uptake as expected.

Figure 5:
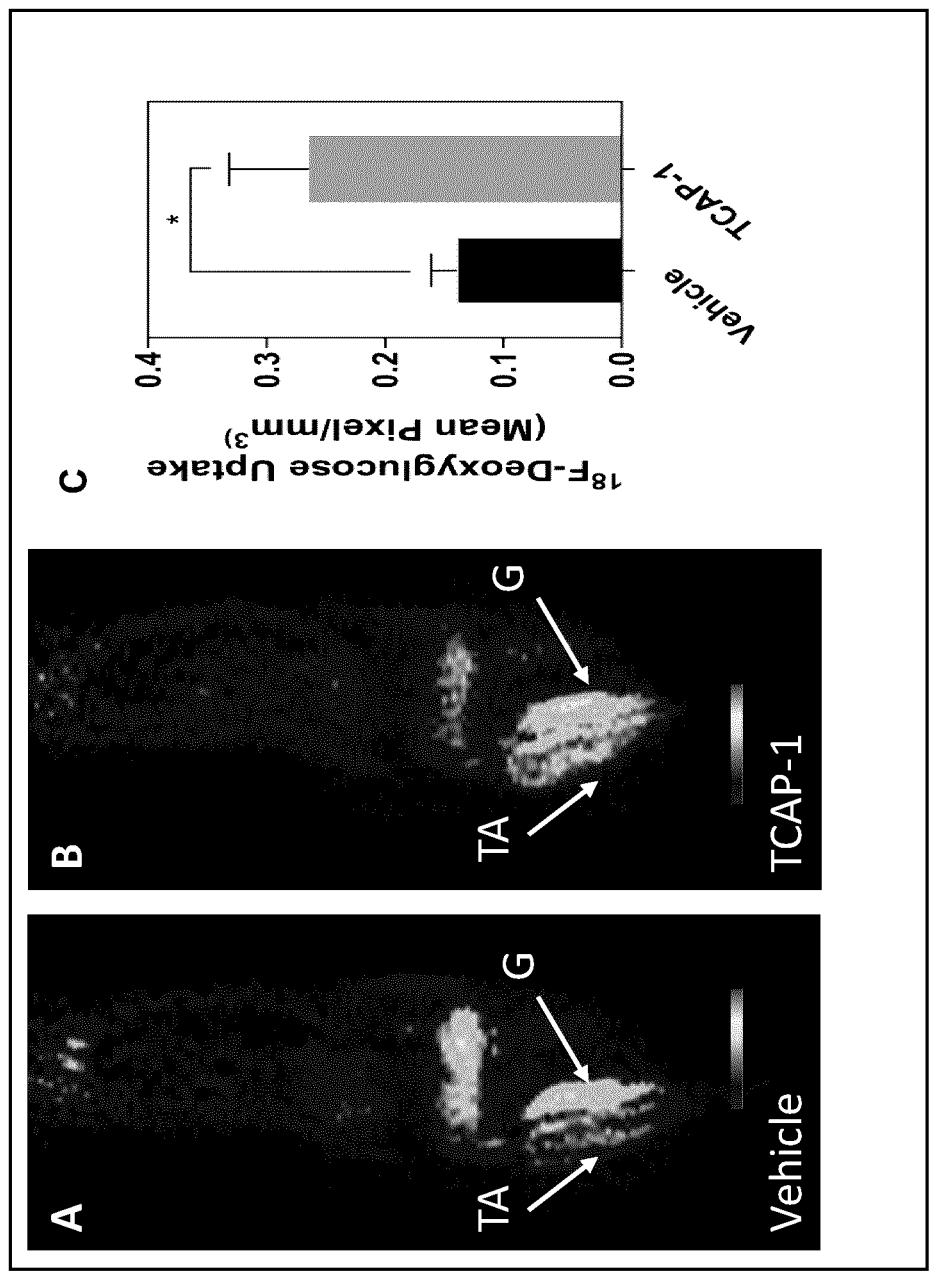
FIG. 5: TCAP-1 significantly increases glucose uptake in skeletal muscle in vivo. Single subcutaneous administration of TCAP-1 in Wistar rats results in significant increase of 18F-deoxyglucose uptake 3 days later in the hind limb muscle by visualization of 3D-functional positron emission tomography (fPET). Representative sagittal view images of 3D-fPET scans of hind limb muscles of a vehicle-treated animal (A) and a TCAP-treated animal (B). Quantification of fPET fluorescence (C) (n=5; student's t-test, *p<0.1)

Example 3: TCAP-1 Treatment Significantly Increases Glucose Uptake in Skeletal Muscle In Vivo Having established a model of TCAP-1 action in vitro, the inventors investigated if this effect is conserved in Wistar rats by injecting the animals with radioactively-labeled deoxyglucose ($^{18}$F-DG) and visualizing the fate of this glucose by using functional positron emission tomography (fPET). These scans were then constructed into 3D-projections, allowing for very accurate depiction of glucose uptake in the muscle specifically (FIG. 5 A, FIG. 5 B). It was shown that a single subcutaneous administration of TCAP-1 (10 nmoles/kg) resulted in a significant increase (p<0.1) in radioactively-labeled deoxyglucose ($^{18}$F-DG) uptake in the hind limb muscles 3 days later as seen by increases in fPET fluorescence (FIG. 5 C).

Example 4: TCAP-1 Treatment Significantly Increases Contractile Characteristics

Figure 6:
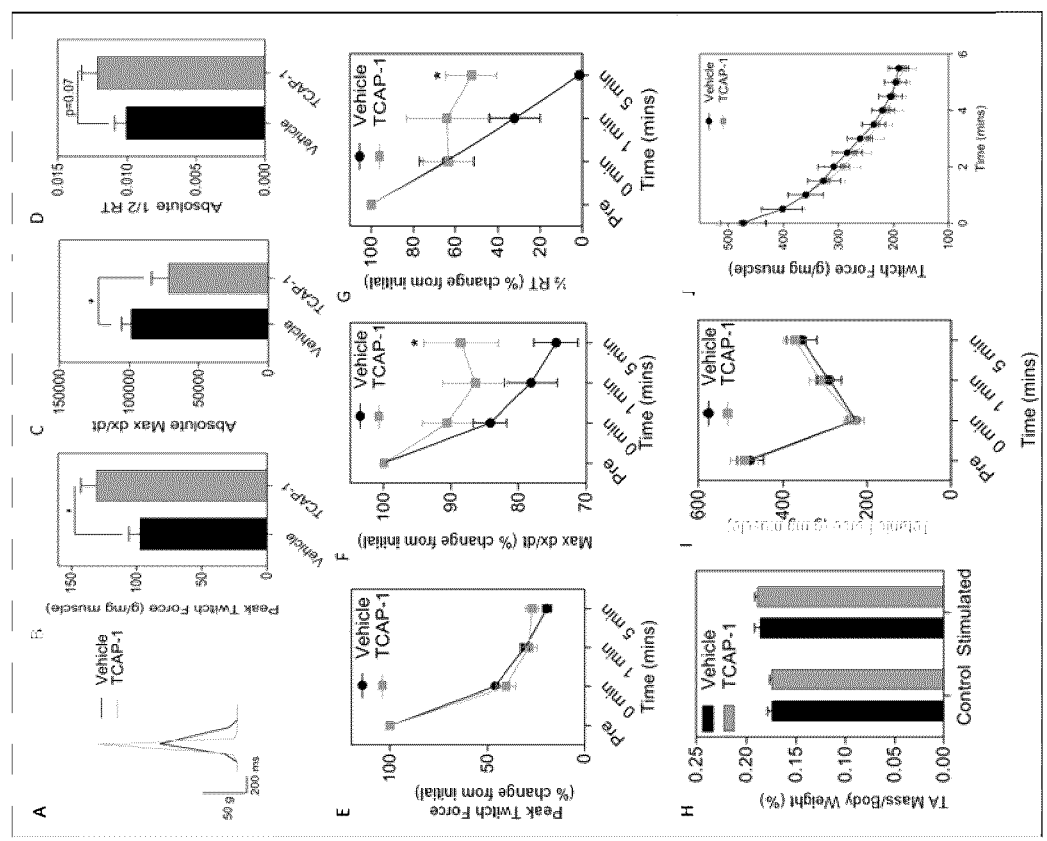
FIG. 6: TCAP-1 administration significantly increases skeletal muscle function via increases in twitch kinetics. Male Sprague-Dawley rats were administered either vehicle (saline) or TCAP-1 (10 nmoles/kg) subcutaneously for 5 consecutive days. Muscle function was tested in vivo 3 days post last injection by electrical stimulation tests of the tibialis anterior muscle. Baseline muscle contractile kinetics of contraction force, contraction velocity, and contraction relaxation rate were tested first. Subsequently, a 6 minute fatigue protocol was electrically induced in the muscle. Muscle contractile kinetics were then again analysed at 0 min, 1 min and 5 min after the fatigue protocol, demonstrating recovery period. Representative twitch traces shown in (A). TCAP-1-treated animals had enhanced baseline contraction kinetics, where it demonstrated significantly increased peak twitch force (B), slower contraction velocity (C), and faster relaxation rate (D) compared to vehicle. TCAP-1-treated animals also demonstrated better recovery, as it had increased peak twitch force (E), and significantly maintained twitch velocity of contraction (F) and rate of relaxation (G) over the fatigue protocol which is not observed in vehicle-treated animals. All data was normalized to muscle weight (n=7-8; 2-way ANOVA, Bonferroni post hoc). Treatment did not affect muscle weight (H), tetanic force (I) or fatigue force curve (J), demonstrating that the effects of TCAP-1 are specific to enhanced muscle function quality.

Male Sprague-Dawley rats were treated for 5 days with either vehicle (saline) or TCAP-1 (10 nmoles/kg) and were tested in a 6-minute fatigue protocol by use of electrical stimulation of the tibialis anterior. Representative twitch traces are shown in FIG. 6 A. Animals treated with TCAP-1 had significantly higher twitch peak force at pre-test (baseline) compared to vehicle-treated animals (p<0.05), FIG. 6 B). As well, the contraction velocity was significantly slower and the contraction relaxation rate was increased in TCAP-1 treated animals (FIG. 6 C, D). After the 6-minute fatigue protocol, TCAP-1 treated animals had a significantly better recovery as; the force generated was increased (FIG. 6 E), the rate of the contractions (max dx/dt) was maintained throughout the protocol whereas the vehicle-treated group showed a steady decline in contraction velocity (p<0.05)

(FIG. 6 F). and the half relaxation time (½RT) was sustained in the TCAP-1-treated animals compared to vehicle (p<0.05) (FIG. 6 G). Extracted muscles from both groups showed no difference in muscle mass (FIG. 6 H) and both groups responded comparably in tetanic force production throughout fatigue or recovery (FIG. 6 I), in the fatigue response curve (FIG. 6 J). Taken together, these results suggest TCAP-1 enhances the quality of the muscle contraction, rather than increasing muscle mass, in order to enhance muscle function. These data demonstrate that TCAP-1 is likely able to maintain contraction cycling efficiency during fatigue, which is lost in vehicle-treated muscles.

Example 5: TCAP-1 Increases the Oxidative Capacity of Skeletal Muscle Fibers

Figure 7:
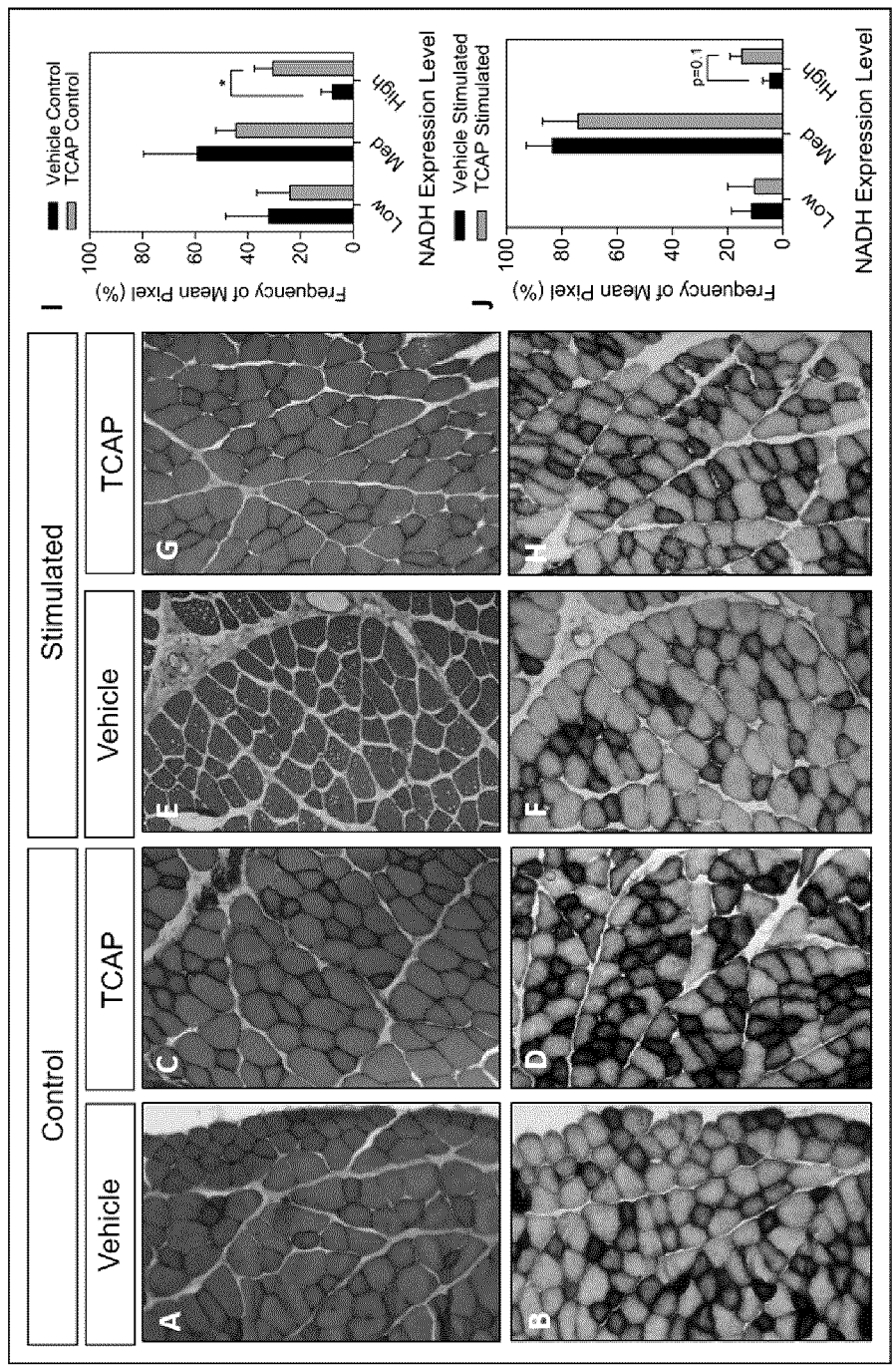
FIG. 7: TCAP-1 increases NADH production of skeletal muscle tissue. Cryosections of tibialis anterior muscle from Sprague-Dawley rats that had been either treated with vehicle (saline) or TCAP-1 (10 nmoles/kg) for 5 days were sectioned and stained for morphology (H&E stain) and NADH stain production (Representative Images of each group A-H). TCAP-1 increases the oxidative capacity of both tissues that were unstimulated (I) and stimulated (J), as seen by the increased frequency of dark fibres, representing increased levels of NADH, a marker of metabolism (n=3, 2-way ANOVA; *p<0.05.

The tibialis anterior is a muscle that is comprised primarily of type II fibers, thus most of the fibers are specialized for glycolysis. As the results above have shown, TCAP-1 increases glucose uptake into the tissue, thus this may be leading to an increase in aerobic metabolism which would be visualized by increases in NADH, a product of Kreb's cycle. Cryosections from the tibialis anterior muscles were analyzed for morphology (FIG. 7 A B C D) and oxidative capacity via NADH staining (FIG. 7 A B C D), a darker grey color representing higher NADH levels. Muscles were taken from the contralateral control (unstimulated) limb as well as the exercised (stimulated) limb. TCAP-1-treated muscles from control limbs showed significant increased frequency of a stronger NADH-positive staining when compared to vehicle-treated muscles (*p<0.05), thus suggesting TCAP-1 increases baseline oxidative capacity in ambient conditions (FIG. 7 E). The TCAP-1-mediated increase in oxidative capacity was also maintained following stimulated conditions as observed in stimulated muscles treated with TCAP-1 compared to vehicle treatment (p=0.1)(FIG. 7 F).

Figure 8:
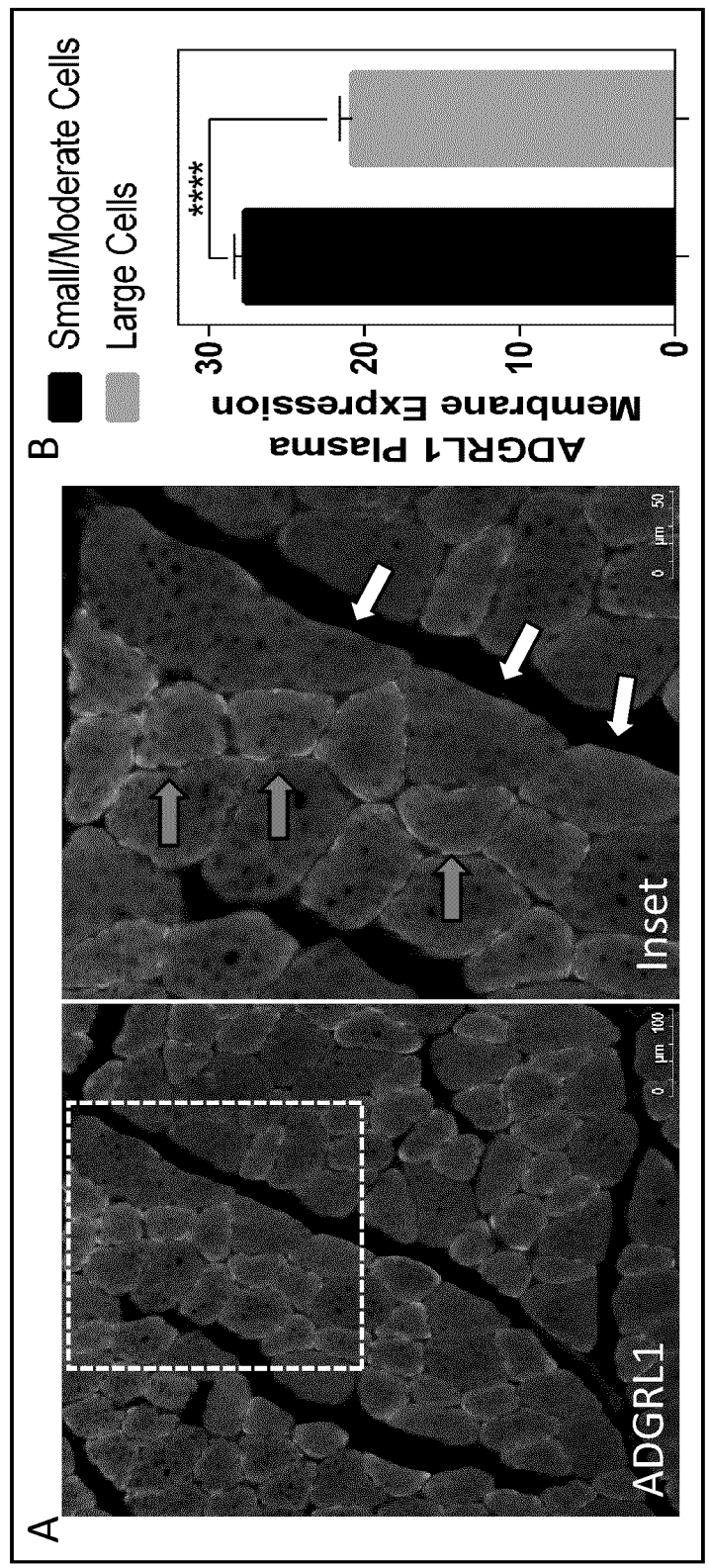
FIG. 8: ADGRL1 expression is significantly higher on membranes of small or moderate sized fibers compared to large sized fibers after TCAP-1 administration. Rat tibialis anterior muscle sections showed a significant increase in ADGRL1 plasma membrane localization of small and moderate sized fibers (gray arrows) compared to large sized fibers (white arrows) (A). Quantification of fluorescence of protein expression (B). Student's t-test, ****p<0.0001 (n=5)

Example 6: ADGRL1 Expression Pattern is Fiber-Specific and Corroborates TCAP-1 Actions The frequency distribution of the oxidative capacity of cells suggested that TCAP-1 was specifically affecting only certain fibers. Thus, further analyses of ADGRL1, the putative receptor for TCAP-1, were done to assess if this pattern of TCAP-1 action was consistent with receptor expression. As the receptor is responsible for ligand action, if the ligand action is fiber-specific it is likely due to receptor specificity. Immunohistochemical analyses of tibialis anterior muscle sections were performed to visualize the ADGRL1 expression. As previously described, the tibialis anterior is comprised mainly of type II fibers, which are broken down into two further types, type IIa/x fibers and type IIb fibers. These two fiber types are both specialized for glycolysis, however, type IIa/x fibers can be more influenced to use aerobic respiration compared to type IIb fibers, and are generally much smaller in diameter. Thus size of fibers was used as a proxy for fiber type to determine if ADGRL1 expression was consistent with fibers that demonstrated TCAP-mediated increases in oxidative capacity (FIG. 8 A). ADGRL1 was found to be significantly higher expressed on small and moderate sized fibers compared to large sized fibers (p<0.0001) (FIG. 8 B), suggesting ADGRL1 is more abundant on type IIa/x fibers. This receptor pattern was consistent with the pattern of TCAP-1 action as determined by oxidative capacity.

Example 7: TCAP-1 Modulates Calcium Cycling in C2C12 Myotubes

To investigate the underlying cellular mechanism of TCAP-1 actions, calcium cycling was analyzed using Fluo-4-AM ester dye in differentiated C2C12 myotubes, where increases in fluorescent intensity indicate increases in cytosolic calcium. As calcium is tightly regulated in myotubes, caffeine was used as a stimulant to release calcium from the sarcoplasmic reticulum as a positive control. To visualize the effects of TCAP-1, cells were pre-treated with TCAP-1 (100 nM) for 1 hour before stimulating with caffeine. When caffeine is applied, the C2C12 myotubes exhibit a strong peak in cytosolic calcium, with gradual decrease over 5 minutes as expected (FIG. 9). When the myotubes were pre-treated with TCAP-1, the caffeine application resulted in a significantly lower peak in cytosolic calcium and resulted in significantly faster decline over 5 minutes (FIG. 9). The results indicate that TCAP-1 treated cells significantly decreased peak calcium as well as returned to baseline calcium levels significantly faster [n=4, 6-7 ROIs per coverslip]. Quantified in (A), representative images shown in (B). This data indicates that TCAP-1 is shuttling the calcium induced by caffeine stimulation out of the cytosol and mediating calcium re-uptake into organelles.

Example 8: TCAP-1 Depolarizes the Mitochondrial Membrane

Figure 10:
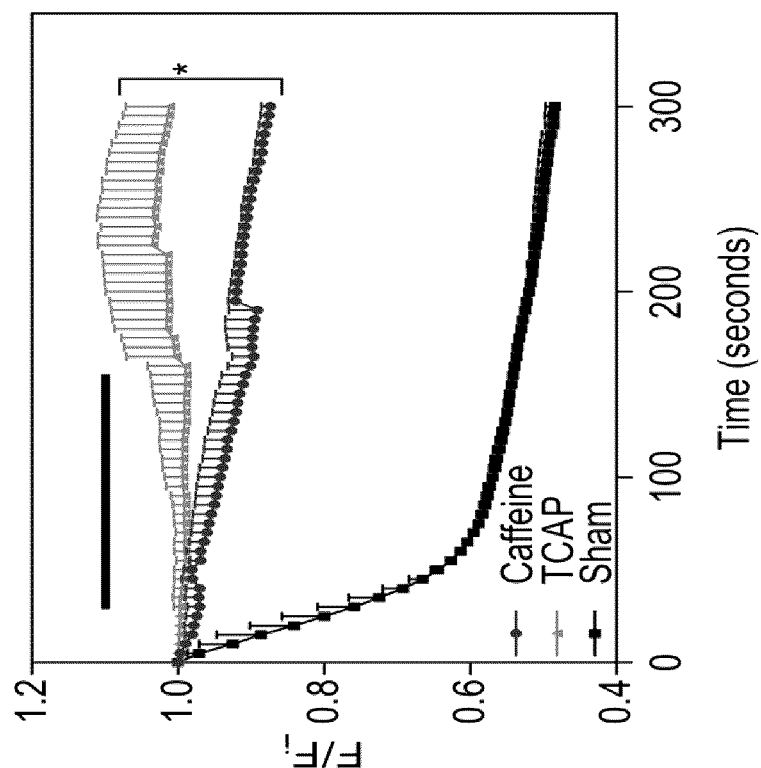
FIG. 10**: TCAP-1 depolarizes the mitochondrial membrane. C2C12 cells were differentiated until Day 6 myotubules and were loaded with Rhodamine-123 (5 uM) which determines changes in mitochondrial membrane potential by relative changes in fluorescence. C2C12 myotubes were either treated with caffeine alone (black circle), or pre-treated with TCAP-1 (100 nM) for 1 hour and subsequently stimulated with caffeine (gray triangle). Cells that were pre-treated with TCAP-1 underwent a significantly higher membrane depolarization than with caffeine alone (n=3, 4-7 ROIs per coverslip; 2-way ANOVA, Tukey's post-hoc test, *p<0.05). Both experimental treatments significantly depolarized mitochondrial membrane compared to sham treatment (black square), which is negative control that does not undergo stimulation.

One candidate organelle of increased TCAP-mediated calcium import is the mitochondria, considering the effect of TCAP-1 on energy and glucose regulation. Within the mitochondria, calcium has stimulatory roles upon enzymes in the Kreb's cycle, as well as upregulates mitobiogenesis. If TCAP-1 was mediating calcium shuttling into the mitochondria, the mitochondrial membrane potential would be affected as result. For these experiments, Rhodamine123 a self-quenching dye was used to measure mitochondrial membrane potential, where an increase in fluorescence indicates membrane depolarization. When caffeine was applied to the C2C12 myotubes, it resulted in mitochondrial membrane depolarization (FIG. 10). When the cells were pre-treated with TCAP-1 (100 nM) for 1 hour before caffeine stimulation, the caffeine application resulted in a significantly higher membrane depolarization compared to caffeine alone (FIG. 10). This data suggests that TCAP-1 modulates mitochondrial activation by depolarizing the mitochondrial membrane via import of calcium, which in turn results in increased energy production.

Discussion

The following non-limiting discussion of the results is provided.

In this work the role of teneurin C-terminal associated peptide (TCAP)-1 was investigated in cell cultures and rodent skeletal muscle. The inventors had to first determine that skeletal muscle contains the required molecular components to induce teneurin/TCAP-ADGRL actions. In recent years, the binding of teneurin and ADGRL has been described in the brain (Boucard et al., 2014; Silva et al., 2011); however, this complex interaction has not been well described in other tissues. Additionally, previous studies have shown that teneurin and TCAP co-localize with the dystroglycan complex in neuronal (Chand et al., 2012) and non-neuronal peripheral tissue (Chand et al., 2014), thus the inventors also investigated if this is conserved in muscle. The presence of the ligand-receptor complex of TCAP, teneurin and ADGRL was successfully established in muscle via genetic expression and protein expression. Moreover, this ligand-receptor complex was also found to be strongly co-localized in skeletal muscle tissue, along with β-dystroglycan, consistent with previous literature. To further show the association with this complex, downstream signaling cascades associated with ADGRL was investigated, such as the PLC-IP3 pathway (Davletov et al., 1998; Rahman et al., 1999). TCAP-1 treatment in immortalized C2C12 cells resulted in a significant decrease in inositol triphosphate (IP3) and diacylglycerol (DAG) levels, which may suggest TCAP-1 is downregulating this pathway. The fact that TCAP-1 can modulate these downstream signaling molecules confirms that TCAP-1 is working through the teneurin/TCAP-ADGRL complex, similar to its role in neurons.

After the characterization of the required molecular components in skeletal muscle, the inventors investigated if the role of TCAP-1 in glucose metabolism in muscle. In neurons, TCAP-1 showed it significantly increases glucose uptake via increases of glucose transporter, GLUT-3, to the plasma membrane in order to facilitate diffusion of glucose into the cell (unpublished). This ultimately leads to increases in ATP production via aerobic pathways, as suggested by decreases in lactate levels. The inventors then investigated the role of TCAP-1 in skeletal muscle metabolism. They first assessed radioactive $^3$H-deoxyglucose uptake in an immortalized murine C2C12 skeletal cell line after TCAP-1 administration, and found a significant increase in glucose uptake after 30 minutes. This finding was replicated in whole animal using functional positron emission tomography (fPET); demonstrating a physiological effect of TCAP-1 on skeletal muscle glucose uptake. There are two potential fates of glucose imported into the muscle; it can either be stored as glycogen, or metabolized to produce energy. Further, glucose metabolism is intrinsically linked to muscle function, as it provides the necessary energy demands of muscle contractions, which steadily decreases in fatigue conditions (Bellinger et al., 2008). The inventors assessed muscle function following TCAP-1 administration by performing in vivo muscle stimulation tests. Importantly, by using electrical stimulation of the muscle the inventors could completely bypass the neurological system of muscle control at the neuromuscular junction. This allowed the inventors to remove variables such as motivation, which is necessary as previous studies have shown that TCAP-1 modulates behavior (Chen et al., 2013; Kupferschmidt et al., 2011).

The results of the muscle function test showed that TCAP-1 treatment significantly increased muscle contractile force, and prolonged contraction velocity and relaxation rate throughout fatigue, indicating improved muscle function compared to vehicle treatment, however showed no difference in muscle mass or fiber size (data not shown). This would suggest that TCAP-1 is increasing the efficiency or quality of the muscle, rather than the quantity of muscle. Therefore, by TCAP-1-mediated increases in glucose uptake, the muscle has a higher energy budget in the fibers and thus allows for continued integrity of muscle contractions which is not observed in vehicle treatments. Further, maintenance of the half relaxation rate throughout fatigue suggests that TCAP-1 is not only regulating glucose but also calcium cycling. Calcium cycling between the sarcomeres and sarcoplasmic reticulum is critical for contraction integrity and becomes aberrant under fatigue conditions (Bellinger et al., 2008). Importantly, there was no difference in tetanic responses of the muscles between TCAP-1 and vehicle treatments (data not shown), thus corroborating that the electrical stimulation protocol induced metabolic fatigue but did not damage the muscle fibers overall.

In order to further elucidate how TCAP-1 is increasing muscle function, the inventors investigated the oxidative capacity of the muscle. As described by Le Châtelier's principle, when a reaction is in equilibrium, an increase of product on one side of the reaction will shift the reaction to increase the other side of the reaction, thereby restoring equilibrium. Thus, as glucose is in equilibrium reaction with pyruvate, TCAP-1-mediated increase in glucose uptake corresponds to an increase in pyruvate production. This in turn could then stimulate aerobic respiration, thus providing the muscle with the necessary energy requirements to meet metabolic demands. When histological analyses of the treated muscles were performed, it demonstrated that TCAP-1 treatment increased oxidative capacity as observed by increases in NADH production, a marker of aerobic respiration, in both control limbs and stimulated (exercised) limbs. This overall increase in the oxidative capacity of the muscle is likely the reason for increased muscle function demonstrated in vivo, as aerobic respiration results in more energy produced per glucose molecule. Interestingly, the muscle used in this study was the tibialis anterior, a muscle comprised of predominantly type II muscle fibers, indicating this muscle is best suited for glycolytic mechanisms; however, TCAP-1 significantly increased its capacity for aerobic metabolism, suggesting TCAP-1 may specifically be affecting type IIa/x fibers, which can be greater influenced to become more oxidative in nature when compared to type IIb fibers.

The pattern of TCAP-1-mediated oxidative capacity suggested that it may work specifically in type IIa/x fibers rather than type IIb fibers. Type IIa/x fibers are generally smaller in size when compared to type IIb fibers, thus using this as a proxy for identification of fibers, the inventors investigated the expression of ADGRL1, the receptor for TCAP-1, to investigate if it has a specific fiber pattern. ADGRL1 expression in skeletal muscle has not been well described, thus it is not known if it is muscle fiber-type specific. ADGRL1 was found in significantly higher proportions in small or moderate sized fibers when compared to large sized fibers, which corroborates the specific pattern of TCAP-1 action. Thus, taken together, this work for the first time demonstrates that the teneurin/TCAP-ADGRL complex is expressed in skeletal muscle, and has a functional role in energy metabolism and muscle function.

Calcium Studies

One major contributor of fatigue in the muscle is the accumulation of calcium in the cytosol due to inefficient cycling of calcium between the sarcoplasmic reticulum and the sarcomeres. As TCAP-1 aids in contractile kinetics, it suggested that TCAP-1 may regulate calcium cycling. Using fluo-4 fluorescent dye as a marker for cytosolic calcium, it was demonstrated that TCAP-1 significantly shuttled calcium back into organelles, and thus out of the cytosol, faster than the positive control caffeine. Moreover, preliminary investigations into where the calcium is being shuttled led to the mitochondria. If calcium was being imported into the mitochondria via the mitochondrial calcium uniporter (MCU), then it would result in a depolarization of mitochondrial membrane. Using Rhodamine123 as a marker for mitochondrial membrane potential, studies showed that mitochondria in C2C12 myotubes were significantly depolarized when pre-treated with TCAP-1 and stimulated with caffeine, more than caffeine only. These data provide critical insight into TCAP-1 actions in the cell and how it translates into its effects in vivo. First, this data corroborates the in vivo muscle performance data as enhanced calcium cycling contributes to enhanced muscle contractile kinetics. Second, direct evidence of TCAP-1 modulating mitochondrial membrane potential indicates TCAP-1 is likely activating the mitochondria. This is line with the previous data showing TCAP-1 affects glucose regulation since activated mitochondria would increase glucose uptake as well as increase ATP output. Thus, TCAP-1 mediating calcium cycling, likely through importing it into mitochondria, is the working model of the mechanism of TCAP-1 action in skeletal muscle. As slowed calcium clearance from the cytoplasm, results in a variety of myopathies, i.e., diseases associated with muscular malfunction, TCAP-1's ability to enhance calcium uptake by the mitochondria to clear calcium from the cytoplasm would have a beneficial application regarding same.

While the foregoing invention has been described in some detail for purposes of clarity and understanding, it will be appreciated by one skilled in the art, from a reading of the disclosure, that various changes in form and detail can be made without departing from the true scope of the invention in the appended claims.

All publications, patents, and patent applications are herein incorporated by reference in their entirety to the same extent as if each individual publication, patent or patent application was specifically and individually indicated to be incorporated by reference in its entirety.

REFERENCES

Anroop B. Nair and Shery Jacob, J Basic Clin Pharm. March 2016-May 2016; 7(2): 27-31 Remington's Pharmaceutical Sciences" by E. W. Martin, 18.sup.th Edition.

Gennaro, ed., Remington: The Science and Practice of Pharmacy, 20th Ed. (Lippincott Williams & Wilkins 2003.

Al Chawaf, A., Xu, K., Tan, L., Vaccarino, F. J., Lovejoy, D. A., & Rotzinger, S. (2007). Corticotropin-releasing factor (CRF)-induced behaviors are modulated by intravenous administration of teneurin C-terminal associated peptide-1 (TCAP-1). http://doi.org/10.1016/j.peptides.2007.05.014

Allen, D. G., Lamb, G. D., & Westerblad, H. (2008). Skeletal muscle fatigue: cellular mechanisms. Physiological Reviews, 88(1), 287-332. http://doi.org/10.1152/physrev.00015.2007.

Bellinger, A. M., Mongillo, M., & Marks, A. R. (2008). Review series Stressed out: the skeletal muscle ryanodine receptor as a target of stress. Journal of Clinical Investigation, 118(2), 445-453. http://doi.org/10.1172/JCI34006.effects Boucard, A. A., Maxeiner, S., & Sudhof, T. C. (2014). Latrophilins function as heterophilic cell-adhesion molecules by binding to teneurins: Regulation by alternative splicing. Journal of Biological Chemistry, 289(1), 387-402. http://doi.org/10.1074/jbc.M113.504779

Chand, D., Song, L., Delannoy, L., Barsyte-Lovejoy, D., Ackloo, S., Boutros, P. C., . . . Lovejoy, D. A. (2012). C-terminal region of teneurin-1 co-localizes with dystroglycan and modulates cytoskeletal organization through an extracellular signal-regulated kinase-dependent stathmin- and filamin A-mediated mechanism in hippocampal cells. Neuroscience, 219, 255-270. http://doi.org/10.1016/j.neuroscience.2012.05.069

Chand, D., Casatti, C. A., de Lannoy, L., Song, L., Kollara, A., Barsyte-Lovejoy, D., . . . Lovejoy, D. A. (2013). C-terminal processing of the teneurin proteins: Independent actions of a teneurin C-terminal associated peptide in hippocampal cells. Molecular and Cellular Neuroscience, 52, 38-50. http://doi.org/10.1016/j.mcn.2012.09.006

Chand, D., Colacci, M., Dixon, K., Kollara, A., Brown, T. J., & Lovejoy, D. A. (2014). C-terminal region of teneurin-1 co-localizes with the dystroglycan complex in adult mouse testes and regulates testicular size and testosterone production. Histochemistry and Cell Biology, 141(2), 191-211. http://doi.org/10.1007/s00418-013-1154-1

Chen, Y., Xu, M., Almeida, R. De, & Lovejoy, D. A. (2013). Teneurin C-terminal associated peptides (TCAP): Modulators of corticotropin-releasing factor (CRF) physiology and behavior. Frontiers in Neuroscience, 7(7 SEP), 1-6. http://doi.org/10.3389/fnins.2013.00166

Davletov, B. A., Meunier, F. A., Ashton, A. C., Matsushita, H., Hirst, W. D., Lelianova, V. G., . . . Ushkaryov, Y. A. (1998). Vesicle exocytosis stimulated by α-latrotoxin is mediated by latrophilin and requires both external and stored Ca2+. EMBO Journal, 17(14), 3909-3920. http://doi.org/10.1093/emboj/17.14.3909

Holwerda, A. M., & Locke, M. (2014). Hsp25 and Hsp72 content in rat skeletal muscle following controlled shortening and lengthening contractions. Applied Physiology, Nutrition, and Metabolism, 39(12), 1380-1387. http://doi.org/10.1139/apnm-2014-0118

Kenzelmann, D., Chiquet-Ehrismann, R., & Tucker, R. P. (2007). Teneurins, a transmembrane protein family involved in cell communication during neuronal development. Cellular and Molecular Life Sciences, 64(12), 1452-1456. http://doi.org/10.1007/s00018-007-7108-9

Kupferschmidt, D. A., Lovejoy, D. A., Rotzinger, S., & Erb, S. (2011). Teneurin C-terminal associated peptide-1 blocks the effects of corticotropin-releasing factor on reinstatement of cocaine seeking and on cocaine-induced behavioural sensitization. British Journal of Pharmacology, 162(3), 574-583. http://doi.org/10.1111/j.1476-5381.2010.01055.x Maher, F., Davies-Hill, T. M., Lysko, P. G., Henneberry, R. C., & Simpson, I. a. (1991). Expression of two glucose transporters, GLUT1 and GLUT3, in cultured cerebellar neurons: Evidence for neuron-specific expression of GLUT3. Molecular and Cellular Neurosciences, 2(4), 351-60. http://doi.org/10.1016/1044-7431(91)90066-W Minet, a D., Rubin, B. P., Tucker, R. P., Baumgartner, S., & Chiquet-Ehrismann, R. (1999). Teneurin-1, a vertebrate homologue of the Drosophila pair-rule gene ten-m, is a neuronal protein with a novel type of heparin-binding domain. Journal of Cell Science, 112 (Pt 1, 2019-2032.

Rahman, M. A., Ashton, A. C., Meunier, F. A., Davletov, B. A., Dolly, J. O., & Ushkaryov, Y. A. (1999). Norepinephrine exocytosis stimulated by alpha-latrotoxin requires both external and stored Ca2+ and is mediated by latrophilin, G proteins and phospholipase C. Philosophical Transactions of the Royal Society of London. Series B, Biological Sciences, 354(1381), 379-86. http://doi.org/10.1098/rstb.1999.0390

Richter, E. A., & Hargreaves, M. (2013). Exercise, glut4, and skeletal muscle glucose uptake, (FIG. 2), 993-1017. http://doi.org/10.1152/physrev.00038.2012

Santos, J. M., Ribeiro, S. B., Gaya, A. R., Appell, H. J., & Duarte, J. A. (2008). Skeletal muscle pathways of contraction-enhanced glucose uptake. International Journal of Sports Medicine, 29(10), 785-794. http://doi.org/10.1055/s-2008-1038404

Silva, J.-P., Lelianova, V. G., Ermolyuk, Y. S., Vysokov, N., Hitchen, P. G., Berninghausen, O., . . . Ushkaryov, Y. A. (2011). Latrophilin 1 and its endogenous ligand Lasso/teneurin-2 form a high-affinity transsynaptic receptor pair with signaling capabilities. Proceedings of the National Academy of Sciences of the United States of America, 108(29), 12113-8. http://doi.org/10.1073/pnas.1019434108

Smerdu, V. et al, "Type IIx myosin heavy chain transcripts are expressed in type IIb fibers of human skeletal muscle" Am. Physiological Society 1994, pp. C1723-C1728.

Tan, L. A., Al Chawaf, A., Vaccarino, F. J., Boutros, P. C., & Lovejoy, D. A. (2011). Teneurin C-terminal associated peptide (TCAP)-1 modulates dendritic morphology in hippocampal neurons and decreases anxiety-like behaviors in rats. Physiology and Behavior, 104(2), 199-204. http://doi.org/10.1016/j.physbeh.2011.03.015

Tan, L. A., Xu, K., Vaccarino, F. J., Lovejoy, D. A., & Rotzinger, S. (2009). Teneurin C-terminal associated peptide (TCAP)-1 attenuates corticotropin-releasing factor (CRF)-induced c-Fos expression in the limbic system and modulates anxiety behavior in male Wistar rats. Behavioural Brain Research, 201, 198-206. http://doi.org/10.1016/j.bbr.2009.02.013

Trubiani, G., Al Chawaf, A., Belsham, D. D., Barsyte-Lovejoy, D., & Lovejoy, D. A. (2007). Teneurin carboxy (C)-terminal associated peptide-1 inhibits alkalosis-associated necrotic neuronal death by stimulating superoxide dismutase and catalase activity in immortalized mouse hypothalamic cells. Brain Research, 1176(1), 27-36. http://doi.org/10.1016/j.brainres.2007.07.087

Uemura, E., & Greenlee, H. W. (2006). Insulin regulates neuronal glucose uptake by promoting translocation of glucose transporter GLUT3. Experimental Neurology, 198(1), 48-53. http://doi.org/10.1016/j.expneurol.2005.10.035

Wang, L., Rotzinger, S., Al Chawaf, A., Elias, C. F., Barsyte-Lovejoy, D., Qian, X., . . . Lovejoy, D. A. (2005). Teneurin proteins possess a carboxy terminal sequence with neuromodulatory activity. Molecular Brain Research, 133(2), 253-265. http://doi.org/10.1016/j.molbrainres.2004.10.019

Woelfle, R., D'Aquila, A. L., Pavlovic, T., Husic, M., Lovejoy, D. A. (2015). Ancient interaction between the teneurin C-terminal associated peptides (TCAP) and latrophilin ligand-receptor coupling: a role in behavior, 9(April), 1-10. http://doi.org/10.3389/fnins.2015.00146

Zurlo, F., Larson, K., Bogardus, C., & Ravussin, E. (1990). Skeletal muscle metabolism is a major determinant of resting energy expenditure. Journal of Clinical Investigation, 86(5), 1423-1427. http://doi.org/10.1172/JCI114857

What is claimed is:

1. A method for enhancing and/or restoring muscle function in a patient in need thereof comprising administering to a patient in need thereof a therapeutically effective amount of a teneurin c-terminal associated peptide-1 (TCAP-1 peptide), or a pharmaceutically acceptable salt or ester thereof or a pharmaceutical composition comprising same, wherein the amino acid sequence of said TCAP-1 peptide consists of:
   (i) an amino acid sequence having at least 95% identity to an amino acid sequence selected from the group consisting of SEQ ID NOs: 1, 2 or 3;
   optionally wherein:
   (a) the carboxy terminal end of said peptide is amidated or comprises an amidation signal sequence; and/or
   (b) when the amino terminal amino acid of said peptide is a glutamine.

2. The method of claim 1 wherein the glutamine is in the form of pyroglutamic acid.

3. The method of claim 1 wherein the TCAP-1 peptide consists of any one of SEQ. ID. NOs: 1, 2 or 3 which is optionally amidated at the carboxy terminal and wherein the glutamine is optionally a pyroglutamic acid at the amino terminal.

4. The method of claim 3 wherein the TCAP-1 is amidated at the carboxy terminal and wherein the glutamine at the amino terminal is a pyroglutamic acid.

5. The method of claim 3 wherein the TCAP-1 is SEQ. ID. NO. 1.

6. The method of claim 3 wherein the TCAP-1 is SEQ. ID. NO. 2.

7. The method of claim 1 wherein the muscle is skeletal muscle.

8. The method of claim 7 wherein TCAP-1 enhances calcium clearance from the cytoplasm or the muscle cell cytosol.

9. The method of claim 1 wherein enhancing and/or restoring muscle function comprises the ability to enhance contractile performance and/or calcium cycling in muscle cells or tissue.

10. The method of claim 1 wherein the enhancing and/or restoring of muscle function comprises restoring calcium cycling and/or for restoring contractile performance in muscle cells.

11. The method of claim 1 wherein enhancing or restoring muscle function comprises one or more of the following: shorter recovery time under muscle fatigue conditions, delayed onset of muscle fatigue, longer ability for muscle to sustain contraction or produce force, increased muscle contractile force, prolonged contraction velocity and relaxation rate during fatigue, increased oxidative capacity, and increased calcium handling/cycling.

12. The method of claim 7 for treating or preventing skeletal muscle atrophy.

13. The method of claim 7 for rehabilitation of skeletal muscle function.

14. The method of claim 1 for reducing muscle recovery time during or after muscle stimulation.

15. The method of claim 14, wherein the stimulation is exercise.

16. The method of claim 1 for reducing or delaying onset of fatigue.

17. The method of claim 8 for enhancing calcium uptake by the mitochondria and or sarcoplasmic reticulum from the cytosol.

* * * * *

```
SEQUENCE LISTING

<160> NUMBER OF SEQ ID NOS: 3

<210> SEQ ID NO 1
<211> LENGTH: 41
<212> TYPE: PRT
<213> ORGANISM: Artificial Sequence
<220> FEATURE:
<223> OTHER INFORMATION: Mouse TCAP1 (41 a.a.)

<400> SEQUENCE: 1

Gln Gln Leu Leu Gly Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile
        35                  40

<210> SEQ ID NO 2
<211> LENGTH: 41
<212> TYPE: PRT
<213> ORGANISM: Artificial Sequence
<220> FEATURE:
<223> OTHER INFORMATION: Human TCAP1 (41 a.a.)

<400> SEQUENCE: 2

Gln Gln Leu Leu Ser Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile
        35                  40

<210> SEQ ID NO 3
<211> LENGTH: 41
<212> TYPE: PRT
<213> ORGANISM: Artificial Sequence
<220> FEATURE:
<223> OTHER INFORMATION: G. gallus TCAP-1

<400> SEQUENCE: 3
```

```
Gln Gln Leu Leu Asn Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile
        35                  40
```